US 8,226,985 B2

(12) United States Patent
Fukushima et al.

(10) Patent No.: US 8,226,985 B2
(45) Date of Patent: Jul. 24, 2012

(54) SURFACE MODIFIED NANOPARTICLES, METHODS OF THEIR PREPARATION, AND USES THEREOF FOR GENE AND DRUG DELIVERY

(75) Inventors: Kazuki Fukushima, San Jose, CA (US); James Lupton Hedrick, Pleasanton, CA (US); Alshakim Nelson, Fremont, CA (US); Daniel Paul Sanders, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 111 days.

(21) Appl. No.: 12/695,991

(22) Filed: Jan. 28, 2010

(65) Prior Publication Data

US 2011/0182996 A1 Jul. 28, 2011

(51) Int. Cl.
- A61K 9/14 (2006.01)
- A61K 48/00 (2006.01)
- A61K 47/00 (2006.01)

(52) U.S. Cl. ............... 424/497; 424/490; 514/772.3

(58) Field of Classification Search .................. None
See application file for complete search history.

(56) References Cited

U.S. PATENT DOCUMENTS

| | | | |
|---|---|---|---|
| 5,338,532 | A | 8/1994 | Tomalia et al. |
| 6,617,418 | B1 | 9/2003 | Magnusson et al. |
| 6,699,724 | B1 | 3/2004 | West et al. |
| 7,556,858 | B2 | 7/2009 | Rasmussen et al. |
| 2004/0127720 | A1 | 7/2004 | Hedrick et al. |
| 2005/0019923 | A1 | 1/2005 | Uchegbu et al. |
| 2005/0048570 | A1* | 3/2005 | Weber et al. ............... 435/7.1 |
| 2007/0244296 | A1 | 10/2007 | Tomalia et al. |
| 2008/0248126 | A1 | 10/2008 | Cheng et al. |
| 2008/0260795 | A1 | 10/2008 | Baughman et al. |
| 2008/0267903 | A1 | 10/2008 | Uchegbu et al. |
| 2008/0268061 | A1* | 10/2008 | Jordan et al. ............... 424/490 |
| 2008/0309857 | A1 | 12/2008 | Lee et al. |
| 2009/0104119 | A1 | 4/2009 | Majoros et al. |
| 2009/0111980 | A1 | 4/2009 | Hafren |
| 2009/0208580 | A1 | 8/2009 | Shi et al. |
| 2010/0015433 | A1 | 1/2010 | Arfsten et al. |

FOREIGN PATENT DOCUMENTS

WO 03033027 4/2003

OTHER PUBLICATIONS

Seow (Functional polycarbonates and their self-assemblies as promising non-viral vectors, 139 J. Controlled Release 40 (2009)).*

Biela, et al., "One-Pot Synthesis of Star-Shaped Aliphatic Polyesters with Hyperbranched Cores and Their Characterization with Size Exclusion Chromatography," J.Polymer Science PartA Polymer Chemistry, vol. 44, 4214-4221 (2006).

Bourissou, et al., "Recent advances in the controlled preparation of poly(a-hydroxy acids): Metal-free catalysts and new monomers," Comptes Rendus Chimie, vol. 10 (2007), 775-794.

Coulembier, et al., "From controlled ring-opening polymerization to biodegradable aliphatic polyester: Especially poly(b-malic acid) derivatives," Prog. Polym. Sci., vol. 31 (2006), 723-747.

Dove, "Controlled ring-opening polymerisation of cyclic esters: polymer blocks in self-assembled nanostructures," Chem. Commun., 2008, 6446-6470.

Jerome, et al., "Recent advances in the synthesis of aliphatic polyesters by ring-opening polymerization," Adv. Drug Delivery Reviews, vol. 60 (2008), 1056-1076.

Kamber, et al., "Organocatalytic Ring-Opening Polymerization", Chem. Rev., 2007, 107, 5813-5840.

Kamber, et al., "N-Heterocyclic Carbenes for the Organocatalytic Ring-Opening Polymerization of #-Caprolactone," Macromolecules, 2009, 42(5), 1634-1639).

Pounder, et al., "Metal free thiol—maleimide 'Click' reaction as a mild functionalisation strategy for degradable polymers", Chem. Commun., 2008, 5158-5160.

Radowski, et al., "Supramolecular Aggregates of Dendritic Multishell Architectures as Universal Nanocarriers," Angew. Chem. Int. Ed. 2007, 46, 1265-1269.

Wiltshire, et al., "Degradable Core Cross-Linked Star Polymers via Ring-Opening Polymerization," Macromolecules, 2006, 39 (13), 4282-4285.

Xiong, et al., "Synthesis of PEG-Armed and Polyphosphoester Core-Cross-Linked Nanogel by One-Step Ring-Opening Polymerization," Macromolecules, 2009, 42 (4), 893-896.

* cited by examiner

*Primary Examiner* — Robert A Wax
*Assistant Examiner* — Sarah Park
(74) *Attorney, Agent, or Firm* — Michael R. Roberts

(57) ABSTRACT

A composition comprises a surface modified nanoparticle comprising a core comprising a material selected from the group consisting of organic materials, organometallic materials, inorganic materials, metals, metal oxides, and combinations thereof; and a surface branch covalently linked to the core having the general formula (3):

(3)

[structure shown]

28 Claims, No Drawings

SURFACE MODIFIED NANOPARTICLES, METHODS OF THEIR PREPARATION, AND USES THEREOF FOR GENE AND DRUG DELIVERY

BACKGROUND

The present invention relates to surface modified nanoparticles, methods of their preparation, and uses thereof for gene and drug delivery, and more specifically, to nanoparticles comprising surface polymers derived by a ring opening reaction.

The emerging field of nanomedicine offers opportunities in health care including curing disease and repairing damaged tissues. Polymers possessing controlled functionalities, molecular weights, polydispersities, molecular architectures and topologies are expected to play essential roles in the transport and delivery of drugs, genes, and other biologically active materials. Synthetic designs are sought that provide specific recognition and targeting capabilities of the carrier-cargo complex. Ultimately, compartmentalized (e.g., layered) nanostructures are desired in which each compartment provides some feature necessary for transport, delivery and/or release of a bio-active cargo.

Numerous polymer carriers have been prepared that are capable of delivering biologically active cargo both in vitro and in vivo, including both dynamic and static assemblies. Dynamic delivery vehicles include micelles, vesicles, liposomes, etc. which self assemble in solution around the drug cargo and are subsequently delivered to the target. These nanostructures are in continuous dynamic equilibrium with the monomeric cargo components. The micelles are constantly dissociating and reassembling, which can be advantageous for cargo release, but limiting to the circulatory lifetime of the complex. A dendrimer is an example of a static, covalently bonded, core-shell system that is limited in cargo capacity and expensive to manufacture. Star-shaped macromolecules circumvent some of these limitations, but star-shaped macromolecular compositions (and synthetic approaches thereto) found in the art offer limited versatility and utility with respect to the transport, delivery and/or release of a bio-active cargo.

A continuing need exists for expanding the scope of macromolecular compositions for gene and drug delivery, and methods of their preparation that provide synthetic design flexibility for tuning carrier properties.

SUMMARY

According to one embodiment of the present invention, a composition comprises a surface modified nanoparticle comprising:

a core comprising a material selected from the group consisting of organic materials, organometallic materials, inorganic materials, metals, metal oxides, and combinations thereof; and a surface branch covalently linked to the core having the general formula (3):

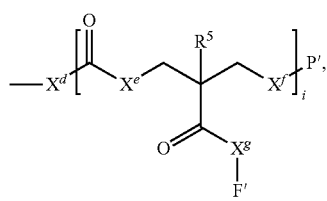

wherein $X^d$ is selected from the group consisting of —O—,

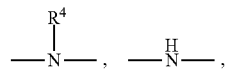

—S—, and combinations thereof, wherein $R^4$ is a monovalent radical comprising 1 to 30 carbons, j is an integer greater than or equal to 1, each of $X^e$, $X^f$, and $X^g$ is independently selected from the group consisting of —O—,

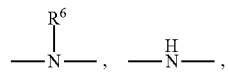

and —S—, wherein $R^6$ is selected from the group consisting of hydrogen and monovalent hydrocarbon radicals comprising 1 to 30 carbons, P' comprises a first polymer comprising a backbone selected from the group consisting of polycarbonates, polyesters, polyureas, polycarbamates, polythiocarbamates, polythioureas, and combinations thereof, each $R^5$ is independently selected from the group consisting of hydrogen, and monovalent hydrocarbon radicals comprising 1 to 30 carbons, and each F' is independently a monovalent radical.

In another embodiment, a method comprises:

independently covalently attaching by a ring opening reaction a first cyclic carbonyl monomer independently to three or more nucleophilic surface groups of a nanostructure, thereby forming a first modified nanoparticle, the first modified nanoparticle comprising three or more initiator groups produced by the ring opening of the first cyclic carbonyl monomer; and independently initiating a ring opening polymerization of a mixture comprising one or more cyclic carbonyl monomers by the three or more initiator groups, thereby forming a surface modified nanoparticle comprising three or more independent surface branches, wherein each of the three or more independent surface branches comprises a first polymer produced by the ring opening polymerization;

wherein the first cyclic carbonyl monomer has the general formula (12):

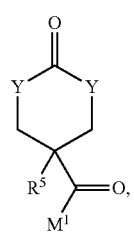

wherein each Y is independently selected from the group consisting of —O—, —NH—,

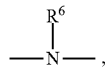

and —S—, $R^5$ and $R^6$ are independent monovalent radicals comprising 1 to 30 carbons, and $M^1$ is is a monovalent radical selected from the group consisting of —$OR^1$, —$NHR^1$, —$NR^1R^1$, and —$SR^1$, wherein $R^1$ is a monovalent radical.

In another embodiment, a method of preparing a loaded nanoparticle, comprises contacting a first aqueous mixture comprising the above described composition with a second aqueous mixture comprising a biologically active material.

In another embodiment, a method comprises:

independently attaching by a ring opening reaction a first cyclic carbonyl monomer to three or more nucleophilic surface groups of a nanostructure, thereby forming a first modified nanoparticle, the first modified nanoparticle comprising three or more functional groups F' and three or more initiator groups; and independently initiating by each of the three or more initiator groups a ring opening polymerization of one or more cyclic carbonyl monomers, thereby forming a surface modified nanoparticle comprising three or more independent surface branches, wherein each of the three or more independent surface branches has the general formula (3):

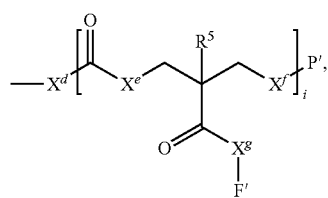

(3)

wherein $X^d$ is a divalent radical selected from the group consisting of —O—,

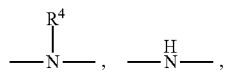

—S—, and combinations thereof, $R^4$ is a monovalent radical comprising 1 to 30 carbons, j is an integer greater than or equal to 1, P' is comprises a first polymer comprising a backbone selected from the group consisting of polycarbonates, polyesters, polyureas, polycarbamates, polythiocarbamates, polythioureas, and combinations thereof, each $X^e$, $X^f$, and $X^g$ is independently selected from the group consisting of —O—,

—S—, and combinations thereof, wherein $R^6$ is hydrogen or a monovalent hydrocarbon radical comprising 1 to 30 carbons, each $R^5$ is independently a monovalent hydrocarbon radical comprising 1 to 30 carbons, and each functional group F' is independently a monovalent radical.

DETAILED DESCRIPTION

Efficient synthetic processes are disclosed for transforming a soft or hard pre-formed nanostructure, comprising a minimum of three nucleophilic surface groups, into a surface modified nanoparticle comprising a tunable functional layer for gene and drug delivery. At least three nucleophilic surface groups of the surface modified nanoparticle are each covalently linked to an independent surface branch comprising a polymer chain derived by ring opening polymerization (ROP) of one or more cyclic carbonyl monomers, referred to herein as a ROP polymer. The ROP polymer can comprise a homopolymer, random copolymer, block copolymer, or combination thereof, and can display amphiphilic properties suitable for loading and carrying a biologically active material, such as a gene or a drug. The nanostructure can comprise a variety of materials, including but not limited to the group consisting of organic materials, organometallic materials, inorganic materials, metals, metal oxides, and combinations thereof. Nanostructures can also comprise clays and organoclays. The three or more nucleophilic surface groups are each capable of ring opening a first cyclic carbonyl monomer, and more particularly a first cyclic carbonate monomer. Exemplary cyclic carbonyl monomers include cyclic esters, cyclic carbonates, and cyclic lactide monomers. Other cyclic carbonyl monomers include cyclic ureas, cyclic carbamates, cyclic thiocarbamates, and cyclic thioureas. A surface branch comprising a ROP polymer is grown in one or more steps from an initiator group formed by a ring opening reaction of the first cyclic carbonyl monomer by a nucleophilic surface group of the nanostructure. The surface branches can be designed to comprise a broad range of pendant functional groups, resulting in "functional layering" of the surface. The functional layers can include, for example, molecular tags/probes, reactive groups for covalently attaching a biologically active cargo (referred to as cargo), groups for releasing a cargo, and/or linear polymers useful in forming reversible complexes with a cargo. Compositions comprising the surface modified nanoparticles are also disclosed.

In particular, each surface branch of the surface modified nanoparticle independently comprises a peripheral first polymer and a linking group that covalently links the peripheral first polymer to a nucleophilic surface group of the nanostructure. The linking groups have a well-defined functionality, and form one of the tunable functional layers of the surface modified nanoparticles, in addition to the core of the nanostructure and the peripheral first polymer. The selection of an appropriate functionalized first cyclic carbonyl monomer for the linking group, and one or more cyclic carbonyl monomers for the peripheral first polymer, which can include the first cyclic carbonyl monomer, allows one to specifically tune the hydrophilic and/or hydrophobic balance, cargo binding properties, and release properties of the surface modified nanoparticles for a given cargo and/or optimization of membrane targeting properties.

The nanostructure is represented by the general formula (1):

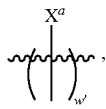
(1)

wherein the wavy line represents the core of the nanostructure, and each $X^a$ is independently covalently linked to the core. The nanostructure comprises w' nucleophilic surface groups $X^a$, wherein w' is greater than or equal to 3. Each $X^a$ is independently selected from the group consisting of —OH, —$NH_2$, —$NHR^4$, —SH, and combinations thereof, wherein $R^4$ is a monovalent radical comprising 1 to 30 carbons. The nanostructure can have a particle size of about 0.1 nm to about 500 nm, 0.1 to 200 nm, 0.1 nm to 100 nm, 0.1 to 50 nm, 0.1 nm to 20 nm, and more particularly, 0.1 to 10 nm.

The surface modified nanoparticle has three or more surface branches. A surface branch has the general formula (2):

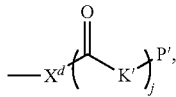
(2)

where it is understood that the dash on the left of $X^d$ indicates the point of attachment to core of the nanostructure. Each $X^d$ is a residue independently derived from one of the three or more nucleophilic groups $X^a$. Each $X^d$ is independently bound to the core (not shown) and a linking group,

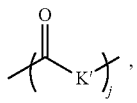

derived from the ring opening of a first cyclic carbonyl monomer. $X^d$ is a divalent radical selected from the group consisting of —O—,

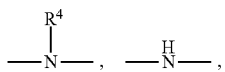

—S—, and combinations thereof, wherein the dashes indicate the point of attachment, and each $R^4$ is independently a monovalent radical comprising 1 to 30 carbons; j is an integer greater than or equal to 1; P' is a peripheral first polymer, also referred to as first polymer, comprising a polymer chain fragment derived by ring opening polymerization of one or more cyclic carbonyl monomers. K' further comprises a functional group F'. When j is 1, from 3 to 20 bonds directly link the carbonyl group and the first polymer P'. When j is greater than 1, each K' can be derived by a ring opening reaction of the first cyclic carbonyl monomer, or a different cyclic carbonyl monomer. In an embodiment, j is 1.

More particularly, a surface branch has the general formula (3):

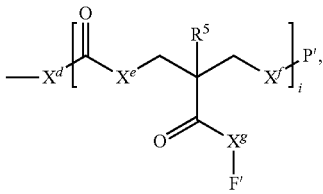
(3)

wherein $X^d$, j, and P' are defined as above; each $X^e$, $X^f$, and $X^g$ are independently selected from the group consisting of —O—,

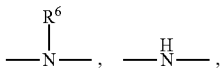

—S—, and combinations thereof, wherein the dashes indicate the point of attachment, and $R^6$ is a monovalent hydrocarbon radical comprising 1 to 30 carbons; each $R^5$ is independently a hydrogen or a monovalent hydrocarbon radical comprising 1 to 30 carbons; and each functional group F' is independently a monovalent radical. Each functional group F' can independently comprise a non-polymeric group or a polymeric group, herein referred to as an optional second polymer. The ring opening polymerization to form the polymer chain fragment (ROP polymer chain) of P' is initiated by an initiator group formed by the ring opening of the first cyclic carbonyl monomer. More particularly, P' comprises a first polymer comprising a backbone type selected from the group consisting of polycarbonates, polyesters, polyureas, polycarbamates, polythiocarbamates, polythioureas, and combinations thereof. The one or more cyclic carbonyl monomers can include the first cyclic carbonyl monomer, if desired. The optional second polymer can also comprise a second ROP polymer chain. P' can further comprise a substituent group selected from the group consisting of urea groups, carboxylic acid groups, carboxylic acid salts, latent carboxylic acid groups, quaternary amine groups, tertiary amine groups, poly(alkylene ether) groups, and combinations thereof. When j is greater than 1, each $R^5$ and each F' can independently comprise the same or different groups. More particularly, each F' can independently comprise a substituent group selected from the group consisting of urea groups, carboxylic acid groups, carboxylic acid salts, latent carboxylic acid groups, quaternary amine groups, tertiary amine groups, poly(alkylene ether) groups, and combinations thereof. In a preferred embodiment, j is 1, and each $X^e$ and $X^f$ is oxygen. In an embodiment, F' comprises a second polymer. In another embodiment, F' is hydrogen. In still another embodiment, F' comprises a poly(alkylene ether) chain, and P' comprises polymer backbone selected from the group consisting of polyester, polycarbonate, and combinations thereof.

The first polymer and the optional second polymer can independently comprise a homopolymer, random copolymer, block copolymer, or a combination thereof. The first polymer and/or the optional second polymer can further independently comprise a chain fragment derived by radical polymerization (e.g., poly(meth)acrylates, poly(meth)acrylamides, polystyrenes), condensation polymerization (e.g., polyamides, polyesters, polyacetals), transesterificatoin polymerization (e.g., polyesters, polycarbonates), ring opening polymerization (e.g., polyethers, polyesters, polycarbonates, polycarbamate, polythiocarbamate, polyurea, and polythiourea), or combinations thereof. The foregoing backbone types are intended to be exemplary and not limiting. As shown further below in Schemes 1 and 2, the first polymer and the second polymer can be attached to the nanostructure in reverse order; that is, the ring opening polymerization to form the first polymer can be initiated prior to or after covalent attachment of the second polymer to the nanostructure.

The first polymer and/or the optional second polymer can independently comprise an optional end cap group (ECG). In an embodiment, the optional end cap group comprises a moiety selected from the group consisting of alkyl ester groups, aryl ester groups, poly(alkylene ether) groups, thiol groups, amine groups, carboxylic acid groups, quaternary amine groups, functional moieties capable of targeting specific cell types, such as galactose and mannose, and combinations thereof A divergent method of forming a surface modified nanoparticle is illustrated by the non-limiting example of Scheme 1, wherein the nanostructure is treated initially with a first cyclic carbonyl monomer that does not comprise a pendant polymer group (i.e., $Fg_1$ does not comprise a polymer).

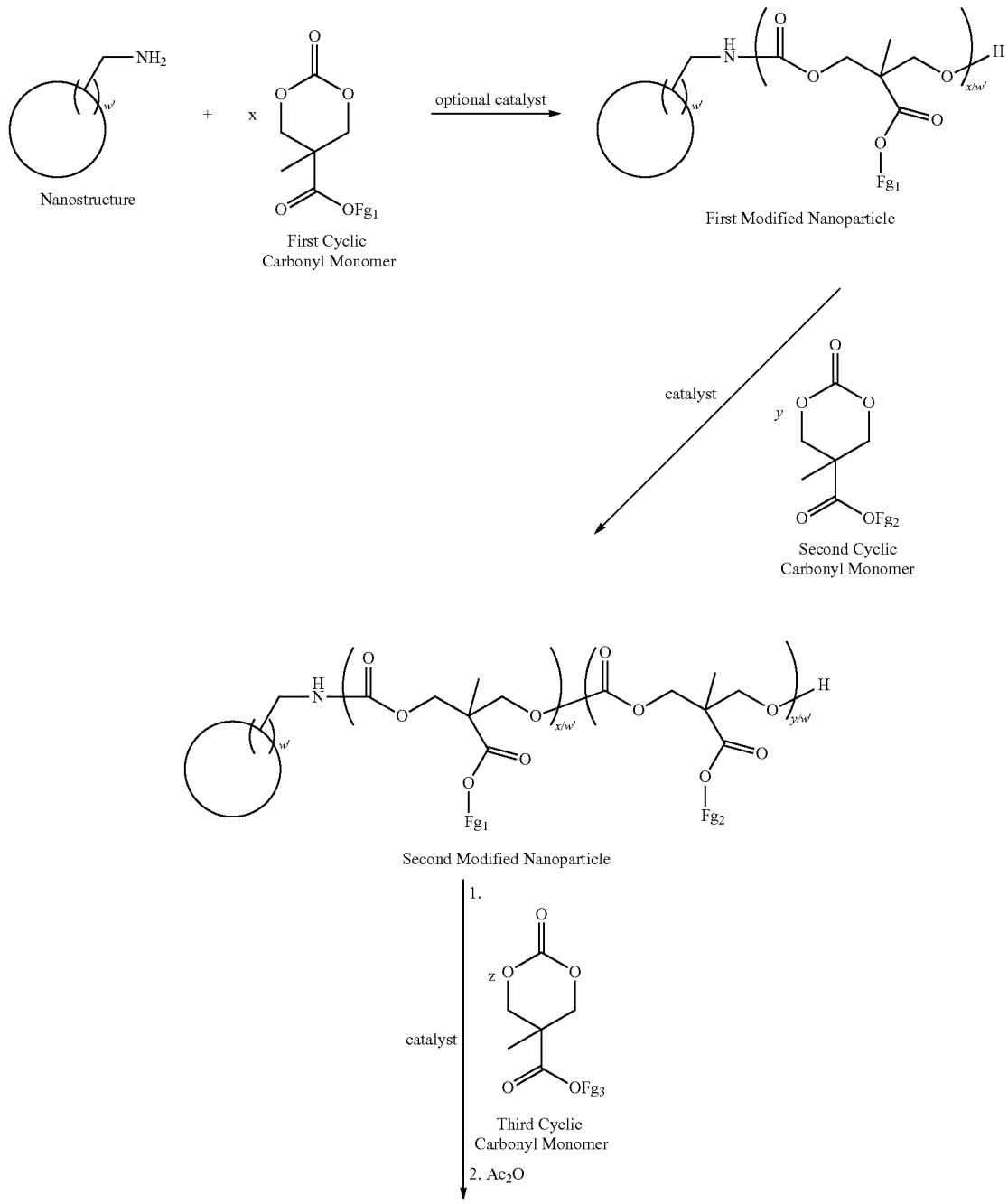

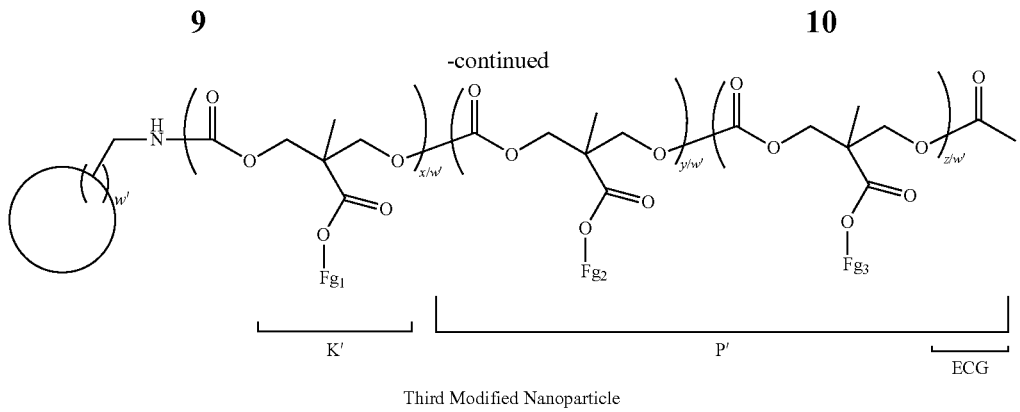

Third Modified Nanoparticle

Accordingly, a nucleophilic surface group is initially reacted with a first cyclic carbonyl monomer in a ring opening reaction to form a first modified nanoparticle, which comprises an initiator group for another ring opening reaction, or a ROP polymerization of one or more cyclic carbonyl monomers, which can include the first cyclic carbonyl monomer. In the example shown, the nanostructure has w' nucleophilic surface groups, where w'≧3. In this example, a second cyclic carbonyl monomer and a third cyclic carbonyl monomer are ring opened sequentially, thereby forming a block copolymer chain, as shown in the second modified nanoparticle and third modified nanoparticle, respectively. K' and P' in Scheme 1 of the third modified nanoparticle correspond to K' and P', respectively, in general formula (2). Alternatively, the second cyclic carbonyl monomer and a third cyclic carbonyl monomer can be combined as a mixture to form a random copolymer chain by ring opening polymerization (not shown). The functional layering arises from the core composition of the nanostructure and the different side chain functional groups $Fg_1$, $Fg_2$, $Fg_3$ ... etc., that can be added to the growing surface branch. Functional groups $Fg_1$, $Fg_2$, $Fg_3$ ... etc. can further be modified after the ring opening reaction. In an embodiment, one or more of the one or more cyclic carbonyl monomers other than the first cyclic carbonyl monomer comprises a poly(alkylene ether) side chain group.

As shown in the example of Scheme 1, the ring opening reaction of the first cyclic carbonyl monomer can be performed with or without a catalyst. In the absence of the catalyst, the primary amine group of the nanostructure reacts by ring opening the first cyclic carbonyl monomer without inducing polymerization (i.e., x/w'=1 in the first modified nanoparticle). When a catalyst is present, the primary amine group of the nanostructure can initiate ring opening polymerization the first cyclic carbonyl monomer (i.e., x is a positive integer multiple of n). In an embodiment, the first ring opening reaction is performed without a catalyst, and without polymerizing the first cyclic carbonyl monomer. In either scenario, the ring opening reaction forms a fragment comprising an initiator group, which can be used for ring opening polymerization (ROP initiator group), and a pendant side chain functional group $Fg_1$. The initiator group in the above example is a hydroxyl group. Each additional ring opening reaction potentially adds a new ROP initiator group to the peripheral end of the growing polymer chain. If desired, the catalyst can be excluded in one or more of the subsequent ring opening reaction steps to add a single ring opened cyclic carbonyl monomer unit at the peripheral end of the growing chain. In this manner, the surface branch can be tailored for many properties, including binding strength to a biologically active material, molecular weight, hydrophilic/hydrophobic balance, membrane recognition, solution stability, biodegradability, and particle size. No limitation is placed on the number of cyclic carbonyl monomers, the number of ring opening steps, the backbone type, the number of polymer blocks, or the side chain functionality, providing that the modified nanoparticle has the desirable carrier properties, which can include cytotoxicity, aqueous dispersion properties, hemolysis properties, and cargo release properties. In an embodiment, the surface branch comprises a first polymer comprising a pendant functional group selected from the group consisting of urea groups, carboxylic acid groups, carboxylic acid salts, latent carboxylic acid groups, quaternary amine groups, tertiary amine groups, and combinations thereof. Other possible functional groups are listed in the cyclic carbonyl monomers of Table 1.

For simplicity, all examples herein assume the ideal case that all w' of the nucleophilic surface groups react and, therefore, the length of polymeric blocks may be described by the division of the number of moles of monomer units (e.g., x, y, z ... etc.) by the number of nucleophilic surface groups (w'). However, the reaction of 100% of the nucleophilic surface groups is not a requirement for successful implementation of the invention. The number of reacted nucleophilic surface groups can be greater than or equal to three and less than or equal to w' when w' is greater than three. In some instances, from more than 0% to less than 100% of the nucleophilic surface groups undergo ring opening reaction with the first cyclic carbonyl monomer. In these instances, the actual length of polymeric blocks can be longer than that calculated for the ideal case (e.g., x/w'). Unreacted nucleophilic surface groups can serve as additional reaction or initiator sites during subsequent synthetic processes. Therefore, it is advantageous that a high percentage of the nucleophilic surface groups undergo the ring opening reaction with the first cyclic carbonyl monomer.

In an embodiment, each ring opening reaction after the first ring opening reaction occurs in the presence of a catalyst, particularly an organic catalyst, resulting in ring opening polymerization. If performed sequentially, the ROP polymer chain comprises a block copolymer. In an embodiment, the ROP block copolymer comprises a polycarbonate backbone. In another embodiment, the ROP block copolymer comprises a polyester backbone. In another embodiment the ROP block copolymer comprises a backbone selected from the group consisting of polycarbonate, polyester, and combinations thereof.

Also shown in Scheme 1 is a polymer chain (third modified nanoparticle), end capped with an acetyl group using acetic anhydride. The optional end cap group can impart stability and useful functionality to the final structure. For example, a more complex end cap group comprising a galactose moiety can potentially be useful in targeting liver cells. End capping agents are numerous, and methods of their use are well established in the polymer art. End capping agents can be selected based on the functionality desired and their intended use. In an embodiment, the surface modified nanoparticle comprises a surface branch wherein the peripheral end unit comprises a quaternary amine. In another embodiment, the peripheral end unit comprises a poly(alkylene ether) chain.

A convergent method of forming a surface modified nanoparticle is illustrated by the non-limiting example of Scheme 2, wherein the nanostructure is treated initially with a first cyclic carbonyl monomer comprising a pendant polymer group (second polymer).

Scheme 2. Convergent Synthetic Approach

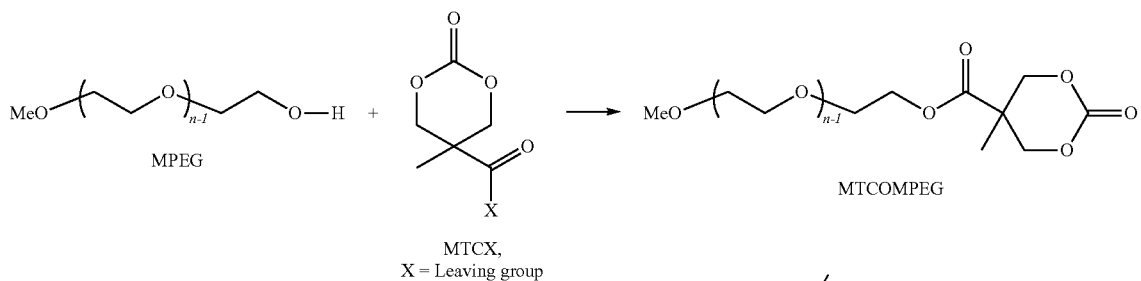

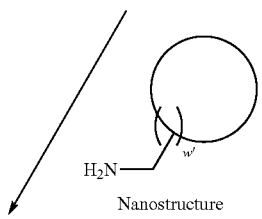

Nanostructure

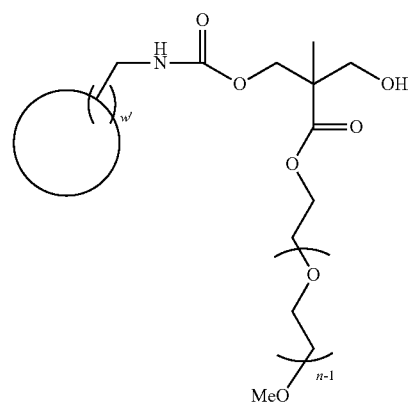

First Modified Nanoparticle

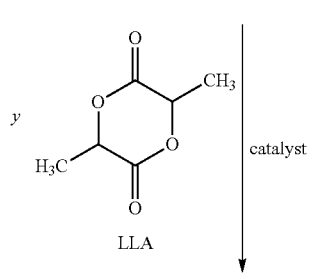

LLA catalyst

-continued

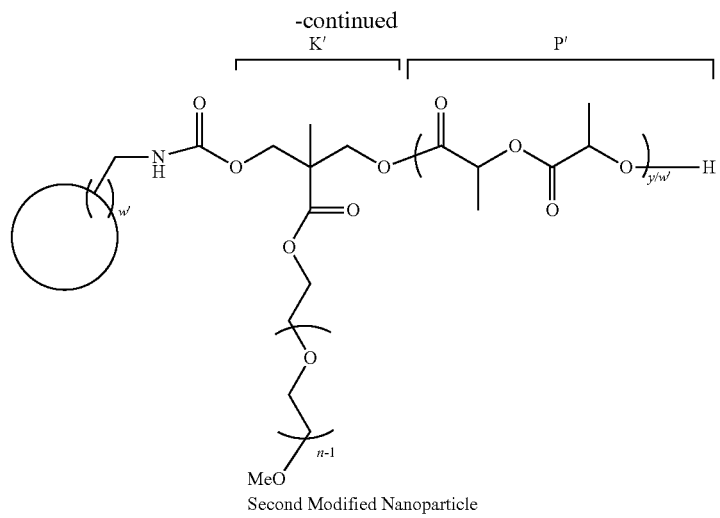

Second Modified Nanoparticle

In the above example, mono-end capped poly(ethylene glycol) (MPEG) is derivatized on the free hydroxyl end by reaction with a cyclic carbonyl compound, MTCX, wherein X is a suitable leaving group, thereby forming the first cyclic carbonyl monomer MTCOMPEG comprising a pendant MPEG group (second polymer). A nanostructure comprising w' nucleophilic surface groups, where w'≧3, undergoes a ring opening reaction with MTCOMPEG, thereby forming a first modified nanoparticle. The first modified nanoparticle comprises an initiator group, in this example a hydroxyl group, capable of initiating ring opening polymerization of a second cyclic carbonyl monomer. In this example, the second cyclic carbonyl monomer is L-lactide (LLA, stereochemistry not shown), and ring opening polymerization of LLA produces a second modified nanoparticle comprising a poly(L-lactide) chain fragment (first polymer). The poly(L-lactide) chain fragment comprises a living end unit (a hydroxyl group) capable of initiating ring opening polymerization of a third cyclic carbonyl monomer, if desired. K' and P' in Scheme 2 correspond to K' and P', respectively, of general formula (2). As shown in this example, the surface branch of the surface modified nanoparticle comprises a hydrophobic poly(L-lactide) polymer fragment (first polymer) and a hydrophilic MPEG polymer fragment (second polymer) that are linked to the nanostructure through the fragment derived from MTCX. The above example is not meant to be restrictive. As stated above, the second polymer can comprise a wide variety of polymer types. In an embodiment, the second polymer comprises a poly(alkylene ether) chain, as shown in Scheme 2. In another embodiment, one or more cyclic carbonyl monomers used in preparing the first polymer comprises a pendant poly(alkylene ether) chain. In another embodiment, the surface branch formed by the convergent method comprises a functional group selected from the group consisting of urea groups, carboxylic acid groups, carboxylic acid salts, latent carboxylic acid groups, quaternary amine groups, tertiary amine groups, and combinations thereof.

The first polymer and/or the second polymer can further comprise an end cap group (e.g., the methoxy group of MPEG (shown)), a living end unit, or a protected end unit that can be deprotected after the ring opening reaction with the nanostructure. The deprotected end unit can comprise, for example, an initiator group for ring opening polymerization of a cyclic carbonyl monomer. Alternatively, the deprotected end unit can be modified to introduce a biologically useful group to the end unit, such as a galactose moiety for liver cell recognition. In an embodiment, the first polymer and/or the second polymer is end capped with a poly(alkeylene ether) chain.

For simplicity, all examples herein assume the ideal case that all w' of the nucleophilic surface groups react and, therefore, the length of polymeric blocks may be described by the division of the number of moles of monomer units (e.g., x, y, z ... etc.) by the number of nucleophilic surface groups (w'). However, the reaction of 100% or the nucleophilic surface groups is not a requirement for successful implementation of the invention. In the case of the convergent approach, only some of the nucleophilic surface groups may react due to steric hindrance by the pendant polymer group attached to the cyclic carbonyl group. In these cases, the actual length of polymeric blocks would longer that that calculated for the ideal case (e.g., x/w'). When w' is greater than three, the number of reacted nucleophilic surface groups can be greater than or equal to three and less than or equal to w'. Unreacted nucleophilic surface groups can serve as additional reaction or initiator sites during subsequent synthetic processes. Therefore, it is advantageous if the degree of reaction of the nucleophilic surface groups is high.

Pre-Formed Nanostructures.

The nanostructure can be selected from a wide variety of materials, with the proviso that the nanostructure has a minimum of three nucleophilic surface groups, and the surface modified nanoparticle has the desired carrier properties, cytotoxicity, biodegradability, hemolytic properties, and/or release properties for a given biologically active cargo. The bulk phase of the nanostructure can comprise, as non-limiting examples, organic material, organometallic material, inorganic material, metal, metal oxide, clay, organoclay, or combinations of the foregoing. A particular inorganic material can be selected from the group consisting of cobalt, iron, and combinations thereof. The organic material can comprise, for example, crosslinked polymers, latexes, hyperbranched polymers, dendrimers, dendrons, cyclodextrins, materials possessing lower critical solution temperature (LCST) transitions in water at from about 0° C. to about 50° C., or combinations of the foregoing materials. The nanostructure can comprise between 3 and 64 (inclusive) or more nucleophilic surface groups. Exemplary nucleophilic surface groups include primary alcohols, secondary alcohols, primary amines, secondary amines, primary thiols, secondary thiols, or combinations of the foregoing functional groups.

In an embodiment, the nanostructure comprises a dendritic polymer material comprising 3 or more nucleophilic surface groups. Dendrimers are monodisperse, tree-like or generational polymer structures prepared in a stepwise process. Dendrimers are constructed one monomer layer, or "generation," at a time. Each dendrimer comprises a multifunctional core molecule, and each functional site of the core molecule has a dendritic wedge attached thereto. The functional sites of the core molecule can be, for example, primary amine groups or another reactive group from which a dendritic wedge can be grown using a step-wise synthetic process. The core molecule is referred to as "generation 0." Each successive repeat unit along all branches forms the next generation, "generation 1," "generation 2," and so on until the nth terminating generation. The terminating generation comprises the nucleophilic surface groups used herein to grow a polymer from the dendrimer surface groups, or attach a pre-formed polymer to the dendrimer surface groups. More particularly, the dendrimer can comprise between 3 and 64 (inclusive) or more nucleophilic surface groups capable of ring opening a first cyclic carbonyl monomer. In a particular embodiment, the first cyclic carbonyl monomer is a cyclic carbonate monomer.

The core molecule from which the dendrimer is derived has the general formula (4):

wherein R' is group comprising from 1 to 20 carbons; each X' is a nucleophilic group independently selected from the group consisting of —OH, —NH$_2$, —NR$^7$, and —SH, and combinations thereof, wherein R$^7$ is a monovalent radical comprising 1 to 30 carbons; and n" is an integer from 2 to 10. R' can comprise a moiety selected from the group consisting of hydrocarbon chains, aliphatic rings, heterocyclic rings, aromatic rings, and combinations thereof. R' can further comprise a functional group selected from the group consisting of ether, amide, ester, secondary amine, tertiary amine, quaternary amine, sulfide, disulfide, sulfonate, urea, carbamate, carbonate, phosphate, phosphonate, and combinations thereof. In an embodiment, the core molecule is a diaminoalkane comprising 2 to 20 carbons.

The first generational growth step adds a minimum of two branches to each X' group of the core molecule. As a non-limiting example, if the core molecule is 1,4-diaminobutane (DAB), each X' is —NH$_2$. The first generation growth step can be the attachment of two aminopropyl groups to each X' group, as follows:

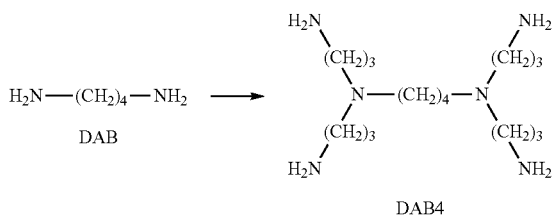

DAB4 is a commercially available first generational polypropylenimine dendrimer, sold by Sigma Aldrich. In a second generation growth step, two aminopropyl chains are attached to each of the four primary amino groups of DAB4, adding four additional branches to the structure, producing DAB8. This process can be repeated for each growth step, doubling the terminal branches in each generation, resulting in a monodisperse structure. Thus, DAB 8, DAB16, DAB32, and DAB64, are the second, third, fourth and fifth generation dendrimers derived from DAB, and have 8, 16, 32 and 64 terminal primary amine groups, respectively.

DAB4 is for illustrative purposes and is not meant to be limiting. Each branch of the dendrimer can independently comprise any of the moieties and/or functional groups defined above for R' of formula (4). More particularly, the dendrimer can comprise branches comprising heteroatoms selected from nitrogen, oxygen, sulfur, phosphorous, and combinations thereof. The outermost branches comprise end groups selected from the group consisting of primary amines, secondary amines, primary alcohols, secondary alcohols, primary thiols, secondary thiols, and combinations of the foregoing, that can react with a cyclic carbonyl monomer by a ring opening reaction.

Other commercially available dendrimers are based on monodisperse polyamidoamines (PAMAM). Surface groups include amidoethanol (—CONH(CH$_2$)$_2$OH), amidoethylethanolamine (—CONH(CH$_2$)$_2$NH(CH$_2$)$_2$OH), amidoamine (—CONH(CH$_2$)$_2$NH$_2$), tris(hydroxymethyl)amidomethane (—CONHCH$_2$(CH$_2$OH)$_3$), bi-functional surface groups comprising amine and hydroxyl groups, and carboxylic acid surface groups. Core molecules used to prepare PAMAM dendrimers include 1,2-ethylenediamine, 1,4-diaminobutane, 1,6-diaminohexane, 1,12-diaminododecane, and cystamine.

Nanostructures can also include polydisperse hyperbranched macromolecules such as those based on 2,2-bis (methylol)propionic acid (bisMPA) chemistry, also commercially available from Sigma Aldrich. These generally have branches comprising polyethers, polyesters, and combinations thereof, and terminal branches comprising primary alcohol groups.

Polyethers.

A polyether chain can provide an important means of introducing hydrophilicity into the surface modified nanoparticle. As stated above, a mono end capped polyether alcohol can be employed as an initiator for ring opening polymerization of a cyclic carbonyl monomer, thereby introducing a main chain hydrophilic block into the resulting ROP polymer.

The polyether alcohol can be a poly(alkylene glycol) of the general formula (5):

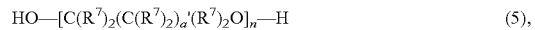

Wherein a' is 0 to 8, n is an integer from 2 to 10000, and each R$^7$ is independently a monovalent radical consisting of hydrogen and an alkyl group of 1 to 30 carbons. Thus, the ether repeat unit comprises 2 to 10 backbone carbons between each backbone oxygen. More particularly, the poly(alkylene glycol) can be a mono endcapped poly(alkylene glycol), represented by the formula (6):

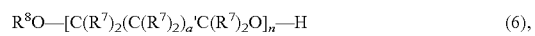

wherein R$^8$ is a monovalent hydrocarbon radical comprising 1 to 20 carbons.

As non-limiting examples, the polyether alcohol can be a poly(ethylene glycol) (PEG), having the structure HO—[CH$_2$CH$_2$O]$_n$—H, wherein the ether repeat unit CH$_2$CH$_2$O (shown in the brackets) comprises two backbone carbons linked to a backbone oxygen. The polyether alcohol can also be a polypropylene glycol) (PPG) having the structure HO—[CH$_2$CH(CH$_3$)O]$_n$—H, where the ether repeat unit CH$_2$CH (CH$_3$)O comprises two backbone carbons linked to a backbone oxygen with a methyl side-chain. An example of mono end capped PEG is the commercially available monomethyl end capped PEG, wherein R$^8$ is a methyl group. Other examples include poly(oxetane), having the structure HO—

[CH₂CH₂CH₂O]$_n$—H, and poly(tetrahydrofuran), having the structure HO—[CH₂(CH₂)₂CH₂O]$_n$—H The mono end capped poly(alkylene glycol) can comprise more elaborate chemical structures, represented by the general formula (7):

$$Z'—[C(R^7)_2(C(R^7)_2)_{a'}C(R^7)_2O]_{n-1}—H \quad (7),$$

wherein Z' is a monovalent radical including the backbone carbons and oxygen of the end repeat unit, and can have 2 to 100 carbons. The following non-limiting examples illustrate mono end-derivatization of poly(ethylene glycol) (PEG). As described above, one end repeat unit of PEG can be capped with a monovalent hydrocarbon group having 1 to 20 carbons, such as the monomethyl PEG (MPEG), wherein Z' is MeOCH₂CH₂O— as shown further above for MPEG in Scheme 2. The dash on the end of the MeOCH₂CH₂O— indicates the point of attachment to the polyether chain. In another example, Z' includes a thiol group, such as HSCH₂CH₂O—, or a thioether group, such as MeSCH₂CH₂O—. In another example, one end unit of PEG is an aldyhyde, wherein Z' can be OCHCH₂CH₂O—. Treating the aldehyde with a primary amine produces an imine, wherein Z' is R⁹N=CHCH₂CH₂O—. R⁹ is a monovalent radical selected from hydrogen, an alkyl group of 1 to 30 carbons, or an aryl group comprising 6 to 100 carbons. Continuing, the imine can be reduced to an amine, wherein Z' is R⁹NHCH₂CH₂CH₂O—. In another example, one end repeat unit of PEG can be oxidized to a carboxylic acid, wherein Z' is HOOCCH₂O—. Using known methods the carboxylic acid can be converted to an ester, wherein Z' becomes R⁹OOCCH₂O—. Alternatively, the carboxylic acid can be converted to an amide, wherein Z' becomes R⁹NHOCCH₂O—. Many other derivatives are possible. In a particular embodiment, Z' is a group comprising a biologically active moiety that interacts with a specific cell type. For example, the Z' group can comprise a galactose moiety which specifically recognizes liver cells. In this instance, Z' has the structure:

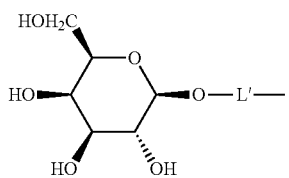

where L' is a divalent linking group comprising 2 to 50 carbons containing the end repeat unit. The hyphen on the right side of L' indicates the attachment point to the polyether chain. Z' can comprise other biologically active moieties such as mannose.

A polyether alcohol employed as an initiator for a ring opening polymerization can comprise a poly(alkylene glycol) or a mono-derivatized poly(alkylene glycol). The polyether alcohol initiator can comprise a mono-derivatized end repeat unit; alternatively, the mono-derivatized end repeat unit can be formed after the ring opening polymerization.

The number average molecular weight of the polyether alcohol can be from 100 to 100,000, more specifically 100 to 10000, and even more specifically, 100 to 5000.

Cyclic Carbonyl Monomers.

The surface branch of the surface modified nanoparticle comprises a polymer chain fragment that in whole or in part is derived by ring opening polymerization of one or more cyclic carbonyl monomers.

A cyclic carbonyl monomer can have the general formula (8):

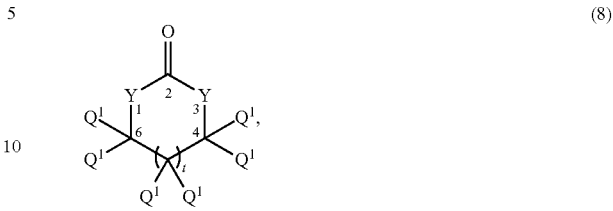

wherein t is an integer from 0 to 6, and when t is 0 carbons labeled 4 and 6 are linked together by a single bond. Each Y is a divalent radical independently selected from the group consisting of —O—, —S—,

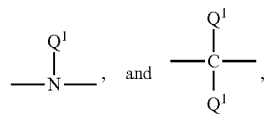

wherein the dashes "-" indicate the point of attachment in the ring. The latter group is also expressed herein as —N(Q¹)- and —C(Q¹)₂—. Each Q¹ is an independent monovalent radical. Each Q¹ group can independently be branched or non-branched. As examples, each Q¹ group can independently be selected from the group consisting of hydrogen, alkyl groups comprising 1 to 100 carbons, and aryl groups comprising 6 to 100 carbons. In an embodiment, at least one Q¹ group is a group other than hydrogen. A Q¹ group can have the structure

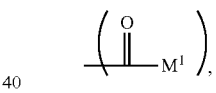

wherein M¹ is a monovalent radical, polymeric or non-polymeric. As examples, each M¹ can independently be selected from the group consisting of —R¹, —OR¹, —NHR¹, —NR¹R¹, and —SR¹ wherein the dash represents the point of attachment, and R¹ is an independent polymeric or non-polymeric monovalent radical. As examples, each R¹ can be independently selected from the group consisting of alkyl groups comprising 1 to 100 carbons, and aryl groups comprising 6 to 100 carbons. Each Q¹ group can further independently comprise one or more additional functional groups selected from the group consisting of ketone groups, aldehyde groups, alkene groups, alkyne groups, cycloaliphatic rings comprising 3 to 10 carbons, heterocylic rings comprising 2 to 10 carbons, ether groups, amide groups, ester groups, carboxylic acid groups, urea groups, and combinations of the foregoing additional functional groups. The heterocyclic ring can comprise oxygen, sulfur and/or nitrogen. Two or more Q¹ groups can together form a ring. In an embodiment, one or more of the Q¹ groups comprises a monovalent urea radical. In another embodiment, one or more of the Q¹ groups comprise a latent carboxylic acid group capable of being converted to a carboxylic acid after ring-opening polymerization. In another embodiment, one or more of the Q¹ groups comprises a functional group capable of reacting with a tertiary amine to form a quaternary amine. In an embodiment, each Q¹ is independently selected from the group consisting of hydrogen, alkyl groups comprising 1 to 100 carbons, and aryl groups comprising 6 to 100 carbons.

A cyclic carbonyl monomer can have the general formula (9):

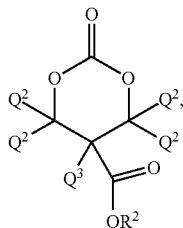

(9)

wherein each $Q^2$ and $Q^3$ is an independent monovalent radical and $R^2$ is a monovalent radical, polymeric or non-polymeric. As examples, each $Q^2$ and $Q^3$ can be independently selected from the group consisting of hydrogen, halides, alkyl groups having 1 to 100 carbons, and aryl groups having 6 to 100 carbons. When $Q^2$ and $Q^3$ are not hydrogen, $Q^2$ and $Q^3$ represent pendant moieties to the cyclic carbonyl ring that become side chains to the ROP polymer chain. The —$CO_2R^2$ group also becomes a side chain to the ROP polymer after ring opening polymerization. In an embodiment, each $Q^2$ is hydrogen and $Q^3$ is a methyl or ethyl group. In an embodiment, $R^2$ comprises a monovalent urea radical. In another embodiment, $R^2$ comprises a latent carboxylic acid group capable of being converted to a carboxylic acid after ring-opening polymerization. In another embodiment, $R^2$ comprises a functional group capable of reacting with a tertiary amine to form a quaternary amine. In yet another embodiment, $R^2$ comprises a second polymer.

A cyclic carbonyl monomer can have the general formula (10):

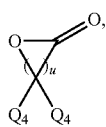

(10)

wherein each $Q^4$ is an independent monovalent radical, and u is an integer from 1 to 8. As examples, each $Q^4$ can independently be selected from the group consisting of hydrogen, halides, alkyl groups comprising 1 to 100 carbons, aryl groups comprising 6 to 100 carbon atoms, and groups having the structure

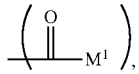

wherein $M^1$ is a monovalent radical, polymeric or non-polymeric. As examples, $M^1$ can be selected from the group consisting of —$R^1$, —$OR^1$, —$NHR^1$, —$NR^1R^1$, and —$SR^1$ wherein the dash represents the point of attachment, and $R^1$ is a monovalent radical, polymeric or non-polymeric. As examples, each $R^1$ can be independently selected from the group consisting of alkyl groups comprising 1 to 100 carbons, and aryl groups comprising 6 to 100 carbons. When $Q^4$ is not hydrogen, $Q^4$ represents a pendant moiety to the cyclic carbonyl ring that becomes a side chain to the ROP polymer after ring opening polymerization. The lactone ring can optionally comprise a carbon-carbon double bond; that is, optionally, a

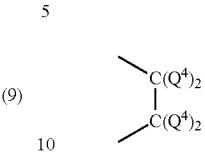

group of formula (10) can independently represent a

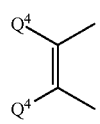

or a

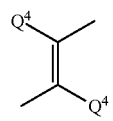

group. The lactone ring can also comprise a heteroatom not linked to the ring carbonyl or ring oxygen, such as oxygen, nitrogen, sulfur, or a combination thereof; that is, optionally a

group of formula (10) can independently represent a —O—, —S—, or —$NR^1$— group. In an embodiment, u is an integer from 1 to 6 and each $Q^4$ is hydrogen. In an embodiment, one or more of the $Q^4$ groups comprises a monovalent urea radical. In another embodiment, one or more of the $Q^4$ groups comprise a latent carboxylic acid group capable of being converted to a carboxylic acid after ring opening polymerization. In another embodiment, one or more of the $Q^4$ groups comprises a functional group capable of reacting with a tertiary amine to form a quaternary amine.

The cyclic carbonyl monomer can have the general formula (11):

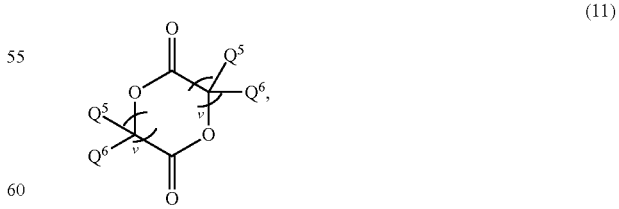

(11)

wherein each $Q^5$ is an independent monovalent radical. As examples, each $Q^5$ can independently be selected from the group consisting of hydrogen, halides, alkyl groups comprising 1 to 100 carbons, aryl groups comprising 6 to 100 carbon atoms, and groups having the structure

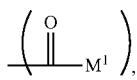

wherein $M^1$ is a monovalent radical, polymeric or non-polymeric, and each v is independently an integer from 1 to 6. As examples, $M^1$ can be selected from the group consisting of —$R^1$, —$OR^1$, —$NHR^1$, —$NR^1R^1$, and —$SR^1$ wherein the dash represents the point of attachment, and $R^1$ is a monovalent radical, polymeric or non-polymeric. As examples, each $R^1$ can be independently selected from the group consisting of alkyl groups comprising 1 to 100 carbons, and aryl groups comprising 6 to 100 carbons. Each $Q^6$ is an independent monovalent radical. As examples, each $Q^6$ can independently be selected from the group consisting of hydrogen, alkyl groups having 1 to 100 carbons, and aryl groups having 6 to 100 carbons. When $Q^5$ and $Q^6$ are not hydrogen, $Q^5$ and $Q^6$ represent pendant moieties to the cyclic carbonyl ring that become side chains to the ROP polymer after ring opening polymerization. In an embodiment, each v is 1, each $Q^5$ is hydrogen, and each $Q^6$ is a hydrocarbon group comprising 1 to 6 carbons. In an embodiment, one or more of the $Q^5$ and/or $Q^6$ groups comprises a monovalent urea radical. In another embodiment, one or more of the $Q^5$ and/or $Q^6$ groups comprises a latent carboxylic acid group capable of being converted to a carboxylic acid after ring-opening polymerization. In another embodiment, one or more of the $Q^5$ and/or $Q^6$ groups comprises a functional group capable of reacting with a tertiary amine to form a quaternary amine.

The first cyclic carbonyl monomer has the general formula (12):

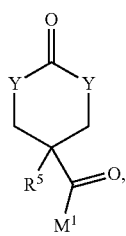

(12)

wherein each Y is independently selected from the group consisting of —O—, —NH—,

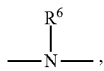

and —S—, $R^5$ and $R^6$ are independent monovalent radicals comprising 1 to 30 carbons, and $M^1$ is selected from the group consisting of —$OR^1$, —$NHR^1$, —$NR^1R^1$, and —$SR^1$ wherein the dash represents the point of attachment, and $R^1$ is a monovalent radical. $M^1$ can comprise a non-polymeric group or a second polymer.

Non-limiting examples of latent carboxylic acids include esters that can be hydrolyzed under mild conditions (e.g., trifluoroethyl ester, pentafluorophenyl ester, or p-nitrophenyl ester, N-hydroxysuccinimimide ester, trimethylsilyl ester, tetrahydropyranyl ester). Other latent carboxylic acids include thermally labile tertiary esters (e.g., t-butyl esters). Still other latent carboxylic acids include esters capable of being reductively cleaved using hydrogen and a suitable catalyst (e.g., benzyl esters, cleavable by $H_2$/Pd—C). In an embodiment, the latent carboxylic acid group is any carboxylic ester that can be converted to a carboxylic acid by hydrogenation using a suitable catalyst. One example is the benzyl ester of MTCOBn.

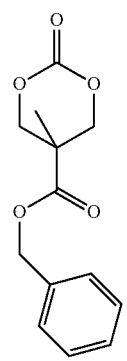

(MTCOBn)

The benzyl ester of MTCOBn can be cleaved to a carboxylic acid using $H_2$/Pd—C after the ring opening polymerization. In another embodiment, a latent carboxylic acid excludes primary or secondary aliphatic hydrocarbon chain esters which cannot be selectively cleaved in the presence of the backbone ester and/or carbonate structures.

Another example of a latent carboxylic acid group is an acetal-protected carboxylic acid group, herein also referred to as an acetal ester group. The acetal ester group has the general formula (13):

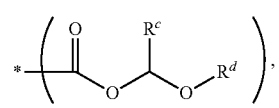

(13)

wherein * represents the site of attachment to a cyclic carbonyl moiety, and $R^c$ and $R^d$ are monovalent radicals independently comprising from 1 to 20 carbons. In an embodiment, $R^c$ is methyl and $R^d$ is ethyl. An example of cyclic carbonyl compound comprising an acetal ester is MTCOEE:

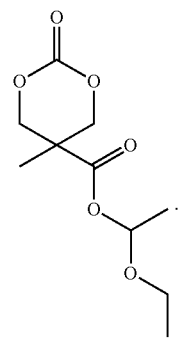

(MTCOEE)

When copolymerized into the polymer, repeat units derived from MTCOEE comprise a side chain acetal ester that is readily deprotected in the acidic endosomal environment. Once released into the cytoplasm, the resulting carboxylic acid groups of the cationic polymer can be deprotonated, Additional cyclic carbonyl monomers of formulas (9), (10), and (11) are listed in Table 1.

TABLE 1

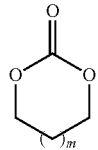

m = 1, Trimethylene carbonate (TMC)
m = 2, Tetramethylene carbonate (TEMC)
m = 3, Pentamethylene carbonate (PMC)

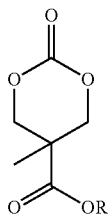

R = hydrogen (MTCOH)
R = methyl (MTCOMe)
R = t-butyl (MTCO$^t$Bu)
R = ethyl (MTCOEt)

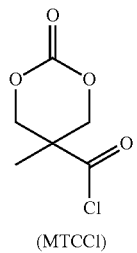

(MTCCl)

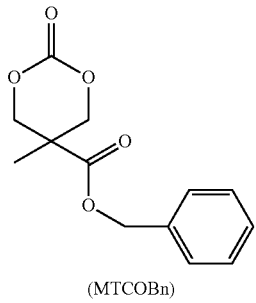

(MTCOBn)

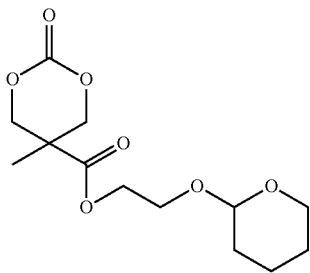

TABLE 1-continued

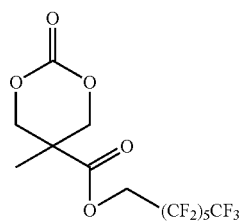

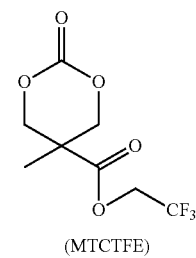

(MTCTFE)

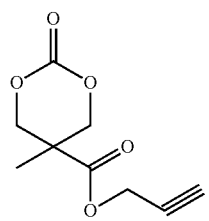

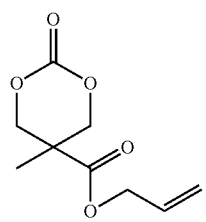

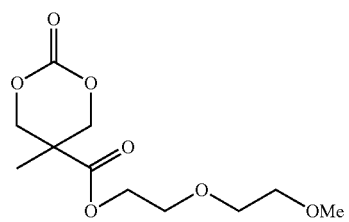

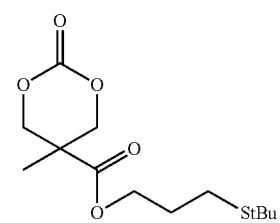

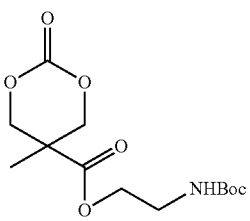

TABLE 1-continued
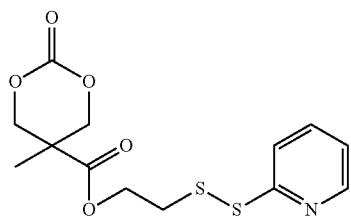
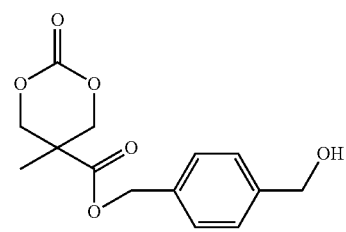
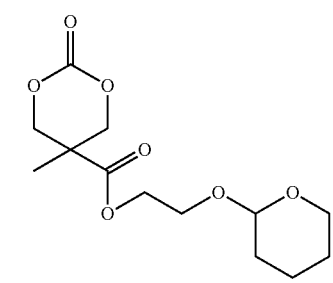
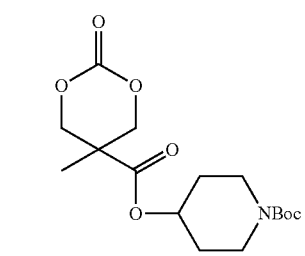
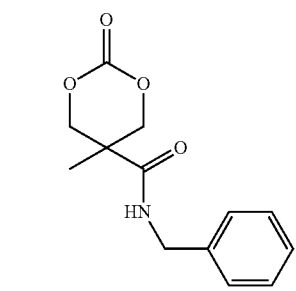
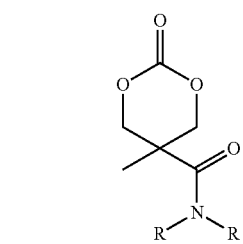
R = methyl
R = iso-propyl
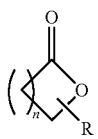
R = H; n = 1: beta-Propiolactone (b-PL)
R = H; n = 2: gamma-Butyrolactone (g-BL)
R = H; n = 3: delta-Valerolactone (d-VL)
R = H; n = 4: epsilon-Caprolactone (e-CL)
R = CH3; n = 1: beta-Butyrolactone (b-BL)
R = CH3; n = 2: gamma-Valerolactone (g-VL)
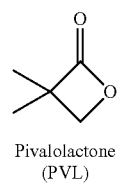
Pivalolactone
(PVL)
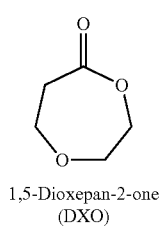
1,5-Dioxepan-2-one
(DXO)
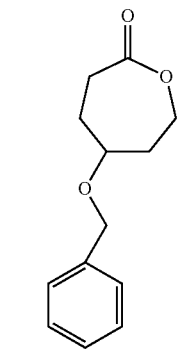
5-(Benzyloxy)oxepan-2-one
(BXO)
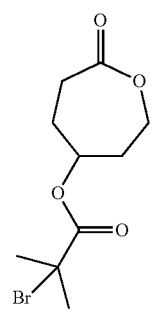
7-Oxooxepan-4-yl 2-bromo-2-methylpropanoate
(BMP-XO)

TABLE 1-continued

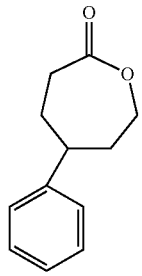

5-Phenyloxepan-2-one
(PXO)

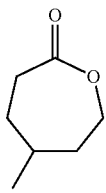

5-Methyloxepan-2-one
(MXO)

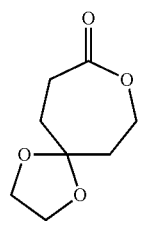

1,4,8-Trioxa(4,6)spiro-9-undecane
(TOSUO)

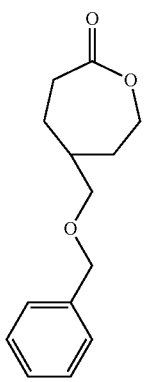

5-(Benzyloxymethyl)oxepan-2-one
(BOMXO)

TABLE 1-continued

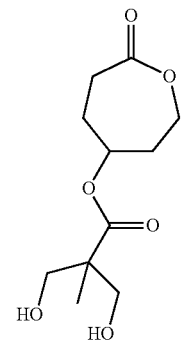

7-Oxooxepan-4-yl 3-hydroxy-2-
(hydroxymethyl)-2-methylpropanoate
(OX-BHMP)

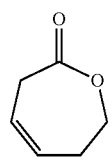

(Z)-6,7-Dihydrooxepin-2(3H)-one
(DHXO)

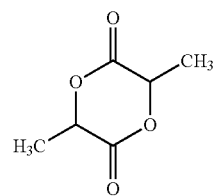

D-Lactide (DLA)
L-Lactide (LLA) or
racemic Lactide, 1:1 D:L forms (DLLA)

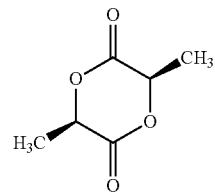

meso-Lactide (MLA)
(two opposite centers of asymmetry
R and S)

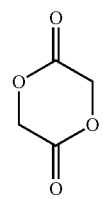

Glycolide
(GLY)

TABLE 1-continued

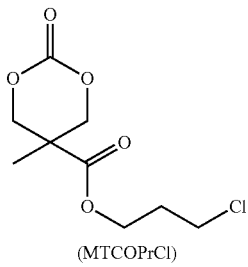

(MTCOPrCl)

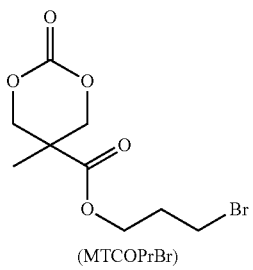

(MTCOPrBr)

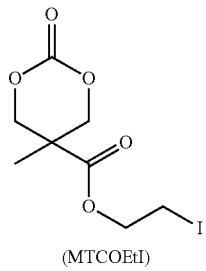

(MTCOEtI)

The cyclic carbonyl monomers can be purified by recrystallization from a solvent such as ethyl acetate or by other known methods of purification, with particular attention being paid to removing as much water as possible from the monomer. The monomer moisture content can be from 1 to 10,000 ppm, 1 to 1,000 ppm, 1 to 500 ppm, and most specifically 1 to 100 ppm, by weight of the monomer.

The cyclic carbonyl monomers can also comprise isotopically enriched forms of the cyclic carbonyl monomers. These include functional groups comprising elements selected from the group consisting of $^{13}$C, $^{14}$C, $^{15}$N, deuterium, tritium, and combinations thereof. The cyclic carbonyl monomers can also comprise a radioactive moiety suitable for targeting a specific cell type, such as a cancer cell. The radioactive moiety can comprise a heavy metal radioactive isotope.

The cyclic carbonyl monomer can comprise a reactive monovalent leaving group that when treated with a tertiary amine, produces a quaternary amine. Reactive monovalent leaving groups include alkyl halides (e.g., alkyl chlorides, alkyl bromides, or alkyl iodides), sulfonate esters (e.g., tosylates, or mesylates), epoxides, and oxetanes. Reaction with the tertiary amine is generally performed after the ring opening reaction when the reactive monovalent leaving group occupies a side chain position in the ROP polymer.

The tertiary amine can comprise a single nitrogen such as a trialkylamine, including but not limited to trimethylamine, triethylamine, tripropylamine, and the like. The tertiary amine can further comprise additional functional groups, in particular a carboxylic acid group, for example 3-(N,N-dimethylamino)propionic acid. In such instances, the cationic polymer will comprise first repeat units comprising a side chain moiety comprising a quaternary amine and a carboxylic acid group.

The tertiary amine can also comprise isotopically enriched versions of the tertiary amine, such as trimethylamine-$^{14}$C, trimethylamine-$^{15}$N, trimethylamine-$^{15}$N, trimethyl-$^{13}$C$_3$-amine, trimethyl-d$_9$-amine, and trimethyl-d$_9$-amine-$^{15}$N. The tertiary amine can also comprise a radioactive moiety suitable for targeting a specific cell type, such as a cancer cell. The radioactive moiety can comprise a heavy metal radioactive isotope.

The tertiary amine can be a bis-tertiary amine of the general formula (14):

(14)

where L" is a divalent linking group comprising 2 to 30 carbons, and each monovalent $R^b$ group is independently selected from alkyl groups comprising 1 to 30 carbons or aryl groups comprising 6 to 30 carbons. Each $R^b$ group can independently be branched or non-branched. Each $R^b$ group can independently comprise additional functional groups such as a ketone group, aldehyde group, hydroxyl group, alkene group, alkyne group, cycloaliphatic ring comprising 3 to 10 carbons, heterocylic ring comprising 2 to 10 carbons, ether group, amide group, ester group, and combinations of the foregoing additional functional groups. The heterocyclic ring can comprise oxygen, sulfur and/or nitrogen. Two or more $R^b$ groups can also together form a ring. Representative L" groups include —(CH$_2$)$_{z'}$— where z' is an integer from 2 to 30, —(CH$_2$CH$_2$O)$_{z''}$CH$_2$CH$_2$— where z" is an integer from 1 to 10, —CH$_2$CH$_2$SCH$_2$CH$_2$—, —CH$_2$CH$_2$SSCH$_2$CH$_2$—, —CH$_2$CH$_2$SOCH$_2$CH$_2$—, and —CH$_2$CH$_2$SO$_2$CH$_2$CH$_2$—. L" can further comprise a monovalent or divalent cycloaliphatic ring comprising 3 to 20 carbons, a monovalent or divalent aromatic ring comprising 6 to 20 carbons, a ketone group, aldehyde group, hydroxyl group, alkene group, alkyne group, a heterocylic ring comprising 2 to 10 carbons, ether group, amide group, ester group, and combinations of the foregoing functional groups. The heterocyclic ring can comprise oxygen, sulfur and/or nitrogen. The bis-tertiary amine can also comprise isotopically enriched forms of the bis-tertiary amine, such as deuterium, carbon-13, and/or nitrogen-15 enriched forms thereof More specific bis-tertiary amines include N,N,N',N'-tetramethyl-1,2-ethanediamine (TMEDA), N,N,N',N'-tetramethyl-1,3-propanediamine (TMPDA), N,N,N',N'-tetramethyl-1,4-butanediamine (TMBDA), N,N,N',N'-tetraethyl-1,2-ethanediamine (TEEDA), N,N,N',N'-tetraethyl-1,3propanediamine (TEPDA), 1,4-bis(dimethylamino) cyclohexane, 1,4-bis(dimethylaminobenzene), N,N,N',N'-tetraethyl-1,4-butanediamine (TEBDA), 4-dimethylaminopyridine (DMAP), 4,4-dipyridyl-1,4-diazabicyclo[2.2.2]octane (DABCO), 4-pyrrolidinopyridine, 1-methylbenzimidazole, and combinations thereof. In an embodiment, the bis-tertiary amine is TMEDA.

The above-described cyclic carbonyl monomers undergo ring-opening polymerization to form a ROP polymers in atactic, syndiotactic or isotactic forms. The particular tacticity depends on the cyclic monomer(s), isomeric purity, and the reaction conditions.

The reaction mixture for the ring opening polymerization comprises one or more cyclic carbonyl monomers; a catalyst; an optional accelerator; an optional solvent, and an initiator. The ring opening polymerization is generally conducted in a reactor under inert atmosphere such as nitrogen or argon. The polymerization can be performed by solution polymerization in an anhydrous non-protic solvent such as benzene, toluene, xylene, cyclohexane, n-hexane, dioxane, chloroform and dichloroethane, or by bulk polymerization. The reaction temperature can be from about ambient temperature to 250° C. Generally, the reaction mixture is heated at atmospheric pressure for 0.5 to 72 hours to effect polymerization, forming a second mixture.

Exemplary catalysts for the ring opening polymerization include metal oxides such as tetramethoxy zirconium, tetra-iso-propoxy zirconium, tetra-iso-butoxy zirconium, tetra-n-butoxy zirconium, tetra-t-butoxy zirconium, triethoxy aluminum, tri-n-propoxy aluminum, tri-iso-propoxy aluminum, tri-n-butoxy aluminum, tri-iso-butoxy aluminum, tri-sec-butoxy aluminum, mono-sec-butoxy-di-iso-propoxy aluminum, ethyl acetoacetate aluminum diisopropylate, aluminum tris(ethyl acetoacetate), tetraethoxy titanium, tetra-iso-propoxy titanium, tetra-n-propoxy titanium, tetra-n-butoxy titanium, tetra-sec-butoxy titanium, tetra-t-butoxy titanium, tri-iso-propoxy gallium, tri-iso-propoxy antimony, tri-iso-butoxy antimony, trimethoxy boron, triethoxy boron, tri-iso-propoxy boron, tri-n-propoxy boron, tri-iso-butoxy boron, tri-n-butoxy boron, tri-sec-butoxy boron, tri-t-butoxy boron, tri-iso-propoxy gallium, tetramethoxy germanium, tetraethoxy germanium, tetra-iso-propoxy germanium, tetra-n-propoxy germanium, tetra-iso-butoxy germanium, tetra-n-butoxy germanium, tetra-sec-butoxy germanium and tetra-t-butoxy germanium; halogenated compound such as antimony pentachloride, zinc chloride, lithium bromide, tin(IV) chloride, cadmium chloride and boron trifluoride diethyl ether; alkyl aluminum such as trimethyl aluminum, triethyl aluminum, diethyl aluminum chloride, ethyl aluminum dichloride and tri-iso-butyl aluminum; alkyl zinc such as dimethyl zinc, diethyl zinc and diisopropyl zinc; tertiary amines such as triallylamine, triethylamine, tri-n-octylamine and benzyldimethylamine; heteropolyacids such as phosphotungstic acid, phosphomolybdic acid, silicotungstic acid and alkali metal salt thereof; zirconium compounds such as zirconium acid chloride, zirconium octanoate, zirconium stearate and zirconium nitrate. More particularly, the catalyst is zirconium octanoate, tetraalkoxy zirconium or a trialkoxy aluminum compound.

Other ROP catalysts include metal-free organocatalysts that can provide a platform to polymers having controlled, predictable molecular weights and narrow polydispersities. Examples of organocatalysts for ring opening polymerization of cyclic esters, carbonates and siloxanes are 4-dimethylaminopyridine, phosphines, N-heterocyclic carbenes (NHC), bifunctional aminothioureas, phosphazenes, amidines, and guanidines. In an embodiment the catalyst is N-(3,5-trifluoromethyl)phenyl-N'-cyclohexyl-thiourea (TU):

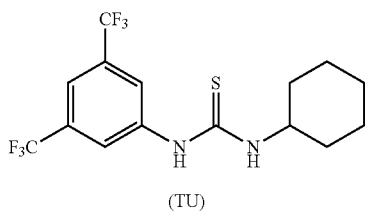

(TU)

In another embodiment, the catalyst and the accelerator are the same compound, such as 1,8-diazabicyclo[5.4.0]undec-7-ene (DBU). Another metal-free ROP catalyst comprises at least one 1,1,1,3,3,3-hexafluoropropan-2-ol-2-yl (HFP) group. Singly-donating hydrogen bond catalysts have the formula (15):

$R^2$ represents a hydrogen or a monovalent radical having from 1 to 20 carbons, for example an alkyl group, substituted alkyl group, cycloalkyl group, substituted cycloalkyl group, heterocycloalkyl group, substituted heterocycloalklyl group, aryl group, substituted aryl group, or a combination thereof. Exemplary singly-donating hydrogen bonding catalysts are listed in Table 2.

TABLE 2

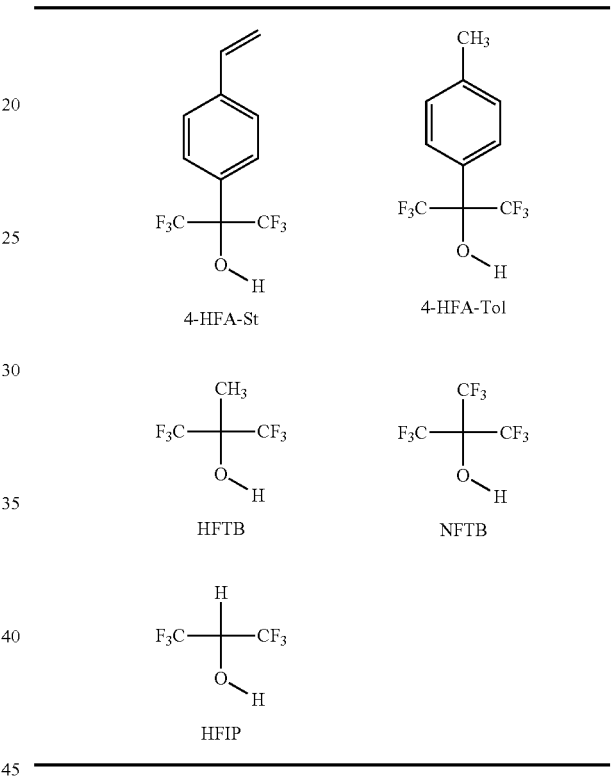

Doubly-donating hydrogen bonding catalysts have two HFP groups, represented by the general formula (16):

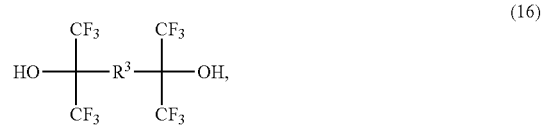

wherein $R^3$ is a divalent radical bridging group containing from 1 to 20 carbons, such as an alkylene group, a substituted alkylene group, a cycloalkylene group, a substituted cycloalkylene group, a heterocycloalkylene group, substituted heterocycloalkylene group, an arylene group, a substituted arylene group, or a combination thereof. Representative double hydrogen bonding catalysts of formula (16) include those listed in Table 3. In a specific embodiment, $R^2$ is an arylene or substituted arylene group, and the HFP groups occupy positions meta to each other on the aromatic ring.

TABLE 3

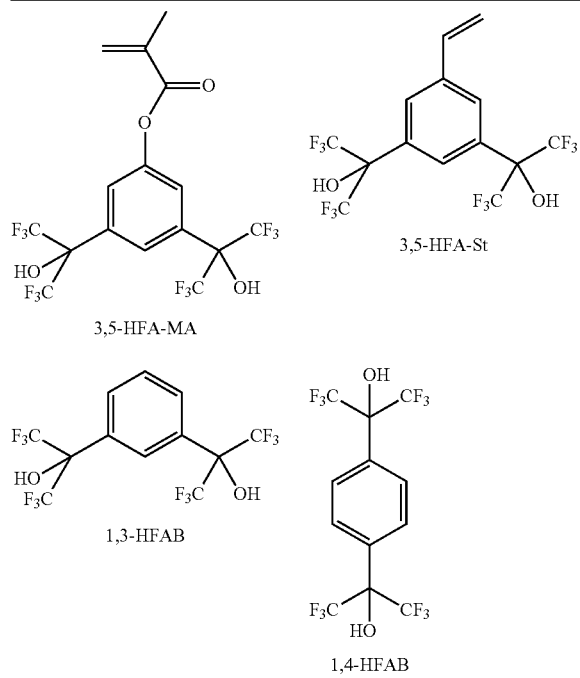

3,5-HFA-MA 3,5-HFA-St 1,3-HFAB 1,4-HFAB

In one embodiment, the catalyst is selected from the group consisting of 4-HFA-St, 4-HFA-Tol, HFTB, NFTB, HPIP, 3,5-HFA-MA, 3,5-HFA-St, 1,3-HFAB, 1,4-HFAB, and combinations thereof Also contemplated are catalysts comprising HFP-containing groups bound to a support. In one embodiment, the support comprises a polymer, a crosslinked polymer bead, an inorganic particle, or a metallic particle. HFP-containing polymers can be formed by known methods including direct polymerization of an HFP-containing monomer (for example, the methacrylate monomer 3,5-HFA-MA or the styryl monomer 3,5-HFA-St). Functional groups in HFP-containing monomers that can undergo direct polymerization (or polymerization with a comonomer) include acrylate, methacrylate, alpha, alpha, alpha-trifluoromethacrylate, alpha-halomethacrylate, acrylamido, methacrylamido, norbornene, vinyl, vinyl ether, and other groups known in the art. Typical examples of such polymerizeable HFP-containing monomers may be found in: Ito et al., *Polym. Adv. Technol.* 2006, 17(2), 104-115, Ito et al., *Adv. Polym. Sci.* 2005, 172, 37-245, Ito et al., US20060292485, Maeda et al. WO2005098541, Allen et al. US20070254235, and Miyazawa et al. WO2005005370. Alternatively, pre-formed polymers and other solid support surfaces can be modified by chemically bonding an HFP-containing group to the polymer or support via a linking group. Examples of such polymers or supports are referenced in M. R. Buchmeiser, ed. "Polymeric Materials in Organic Synthesis and Catalysis," Wiley-VCH, 2003, M. Delgado and K. D. Janda "Polymeric Supports for Solid Phase Organic Synthesis," *Curr. Org. Chem.* 2002, 6(12), 1031-1043, A. R. Vaino and K. D. Janda "Solid Phase Organic Synthesis: A Critical Understanding of the Resin", *J. Comb. Chem.* 2000, 2(6), 579-596, D. C. Sherrington "Polymer-supported Reagents, Catalysts, and Sorbents: Evolution and Exploitation—A Personalized View," *J. Polym. Sci. A. Polym. Chem.* 2001, 39(14), 2364-2377, and T. J. Dickerson et al. "Soluble Polymers as Scaffold for Recoverable Catalysts and Reagents," *Chem. Rev.* 2002, 102(10), 3325-3343.

Examples of linking groups include $C_1$-$C_{12}$ alkyl, $C_1$-$C_{12}$ heteroalkyl, an ether group, a thioether group, an amino group, an ester group, an amide group, or a combination thereof. Also contemplated are catalysts comprising charged HFP-containing groups bound by ionic association to oppositely charged sites on a polymer or a support surface.

The ROP reaction mixture comprises at least one catalyst and, when appropriate, several catalysts together. The ROP catalyst is added in a proportion of 1/20 to 1/40,000 moles relative to the cyclic carbonyl monomers, and preferably of 1/100 to 1/20,000 moles.

The ring-opening polymerization is generally conducted in the presence of an accelerator, in particular a nitrogen base. Exemplary nitrogen base accelerators are listed below and include pyridine (Py), N,N-dimethylaminocyclohexane (Me$_2$NCy), 4-N,N-dimethylaminopyridine (DMAP), trans 1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), 7-methyl-1,5,7-triazabicyclo[4.4.0]dec-5-ene (MTBD), (−)-sparteine, (Sp) 1,3-bis(2-propyl)-4,5-dimethylimidazol-2-ylidene(Im-1), 1,3-bis(2,4,6-trimethylphenyl)imidazol-2-ylidene (Im-2), 1,3-bis(2,6-di-i-propylphenyl(imidazol-2-ylidene (Im-3), 1,3-bis(1-adamantyl)imidazol-2-ylidene (Im-4), 1,3-di-i-propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis(2,6-di-i-propylphenyl)-4,5-dihydroimidazol-2-ylidene, 1,3-bis(2,6-di-i-propylphenyl)-4,5-dihydroimidazol-2-ylidene (Im-8) or a combination thereof, shown in Table 4.

TABLE 4

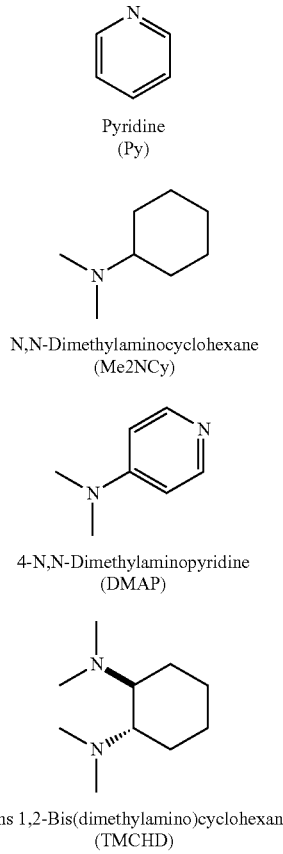

Pyridine
(Py)

N,N-Dimethylaminocyclohexane
(Me2NCy)

4-N,N-Dimethylaminopyridine
(DMAP)

trans 1,2-Bis(dimethylamino)cyclohexane
(TMCHD)

TABLE 4-continued

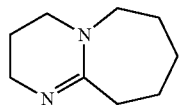

1,8-Diazabicyclo[5.4.0]undec-7-ene
(DBU)

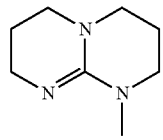

7-Methyl-1,5,7-triazabicyclo[4.4.0]dec-5-ene
(MTBD)

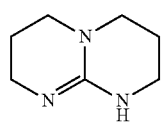

1,5,7-Triazabicyclo[4.4.0]dec-5-ene
(TBD)

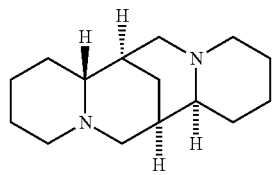

(−)-Sparteine
(Sp)

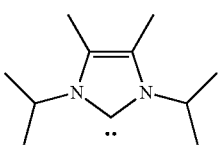

1,3-Bis(2-propyl)-4,5-dimethylimidazol-2-ylidene
(Im-1)

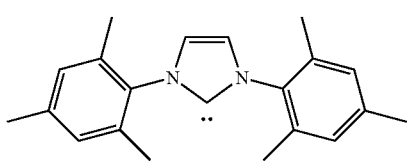

1,3-Bis(2,4,6-trimethylphenyl)imidazol-2-ylidene
(Im-2)

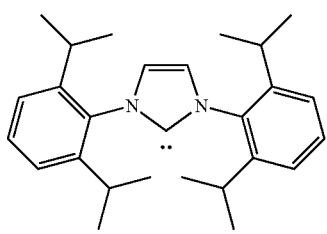

1,3-Bis(2,6-di-i-propylphenyl(imidazol-2-ylidene
(Im-3)

TABLE 4-continued

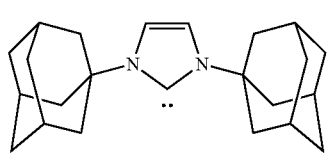

1,3-Bis(1-adamantyl)imidazol-2-yliden)
(Im-4)

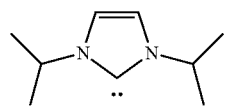

1,3-Di-i-propylimidazol-2-ylidene
(Im-5)

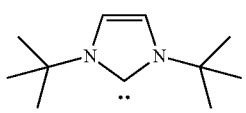

1,3-Di-t-butylimidazol-2-ylidene
(Im-6)

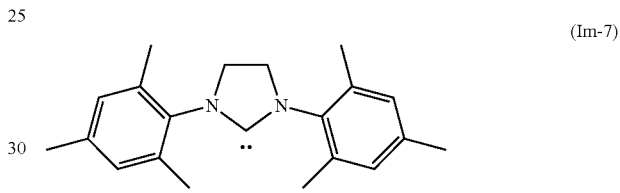

1,3-Bis(2,4,6-trimethylphenyl)-4,5-dihydroimidazol-2-ylidene
(Im-7)

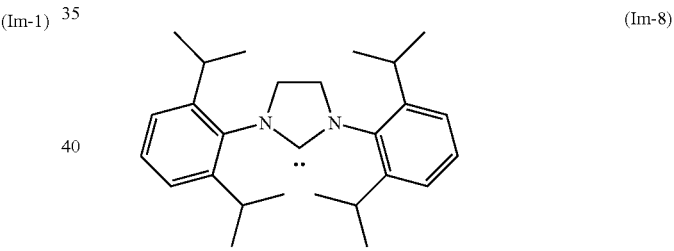

1,3-Bis(2,6-di-i-propylphenyl)-4,5-dihydroimidazol-2-ylidene
(Im-8)

In an embodiment, the accelerator has two or three nitrogens, each capable of participating as a Lewis base, as for example in the structure (−)-sparteine. Stronger bases generally improve the polymerization rate.

The ROP reaction mixture also comprises an initiator. Initiators generally include nucleophiles such as alcohols, amines and thiols. The initiator can be monofunctional, difunctional, or multifunctional. The nanostructure, as well as the surface modified nanoparticle comprising three or more peripheral ROP initiator groups, are examples of multifunctional initiators.

More particularly, the initiator for the ring opening reaction is an alcohol. When a ROP polymer is prepared prior to attachment to the nanostructure, the alcohol initiator can be any suitable alcohol, including mono-alcohol, diol, triol, or other polyol, with the proviso that the choice of alcohol does not adversely affect the polymerization yield, polymer molecular weight, complexation with a bio-active material, and/or the desirable mechanical and physical properties of the surface modified nanoparticle. The alcohol can be multi-functional comprising, in addition to one or more hydroxyl groups, a halide, an ether group, an ester group, an amide group, or other functional group. Exemplary alcohols includes methanol, ethanol, propanol, butanol, pentanol, amyl alcohol, capryl alcohol, nonyl alcohol, decyl alcohol, undecyl alcohol, lauryl alcohol, tridecyl alcohol, myristyl alcohol, pentadecyl alcohol, cetyl alcohol, heptadecyl alcohol, stearyl alcohol, nonadecyl alcohol and other aliphatic saturated alcohols, cyclopentanol, cyclohexanol, cycloheptanol, cyclooctanol and other aliphatic cyclic alcohols; phenol, substituted phenols, benzyl alcohol, substituted benzyl alcohol, benzenedimethanol, trimethylolpropane, a saccharide, poly(ethylene glycol), propylene glycol, alcohol functionalized block copolymers derived from oligomeric alcohols, alcohol functionalized branched polymers derived from branched alcohols, or a combination thereof. Monomeric diol initiators include ethylene glycols, propylene glycols, hydroquinones, and resorcinols. An example of a diol initiator is BnMPA, derived from 2,2-dimethylol propionic acid.

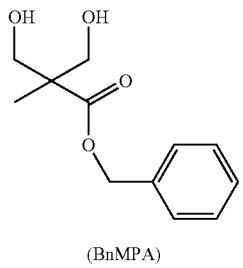

(BnMPA)

BnMPA is a precursor used in the preparation of cyclic carbonate monomers.

The ring-opening polymerization can be performed with or without the use of a solvent, more particularly with a solvent. Optional solvents include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. When a solvent is present, a suitable cyclic carbonyl monomer concentration is about 0.1 to 5 moles per liter, and more particularly about 0.2 to 4 moles per liter. In a specific embodiment, the reaction mixture for the ring-opening polymerization is free of a solvent.

The ring-opening polymerization can be performed at a temperature that is about ambient temperature or higher, more specifically a temperature from 15° C. to 200° C., and more particularly 20° C. to 200° C. When the reaction is conducted in bulk, the polymerization is performed at a temperature of 50° C. or higher, and more particularly 100° C. to 200° C. Reaction times vary with solvent, temperature, agitation rate, pressure, and equipment, but in general the polymerizations are complete within 1 to 100 hours.

Whether performed in solution or in bulk, the polymerizations are conducted in an inert (i.e., dry) atmosphere and at a pressure of from 100 to 500 MPa (1 to 5 atm), more typically at a pressure of 100 to 200 MPa (1 to 2 atm). At the completion of the reaction, the solvent can be removed using reduced pressure.

The nitrogen base accelerator is present in an amount of 0.1 to 5.0 mol %, 0.1 to 2.5 mol %, 0.1 to 1.0 mol %, or 0.2 to 0.5 mol %, based on total moles of cyclic carbonyl monomer.

The amount of initiator is calculated based on the equivalent molecular weight per nucleophilic initiating group in the initiator (e.g., alcohol groups). The initiating groups are present in an amount of 0.001 to 10.0 mol %, 0.1 to 2.5 mol %, 0.1 to 1.0 mol %, and 0.2 to 0.5 mol %, based on total moles of cyclic carbonyl monomer. For example, if the molecular weight of the initiator is 100 g/mole and the initiator has 2 hydroxyl groups, the equivalent molecular weight per hydroxyl group is 50 g/mole. If the polymerization calls for 5 mol % hydroxyl groups per mole of monomer, the amount of initiator is 0.05×50=2.5 g per mole of monomer.

In a specific embodiment, the catalyst is present in an amount of about 0.2 to 20 mol %, the nitrogen base accelerator is present in an amount of 0.1 to 5.0 mol %, and the hydroxyl groups of the initiator are present in an amount of 0.1 to 5.0 mol % based on the equivalent molecular weight per nucleophilic group in the initiator.

As stated above, the ring opening polymerization forms a polymer chain comprising a living polymer segment. In an embodiment, one backbone repeating unit of the ROP polymer chain is a carbonate repeating unit. The ROP polymer backbone can, for example, comprise a polyester homopolymer, a random polyester copolymer, a polycarbonate homopolymer, a random polycarbonate copolymer, or a random polyestercarbonate copolymer. The ROP polymer chain can comprise a terminal hydroxyl group, terminal thiol group, or terminal amine group, each of which can initiate further ROP chain growth, if desired.

The ROP polymer can comprise hydrophilic repeat units, hydrophobic repeat units, and combinations thereof, thereby imparting amphiphilic properties to the surface modified nanoparticles. The ROP polymer chains can have a number average molecular weight $M_n$ as determined by size exclusion chromatography of at least 2500 g/mol, more specifically 4000 g/mol to 150000 g/mol, and even more specifically 10000 g/mol to 50000 g/mol. In an embodiment, the ROP polymer chain has a number average molecular weight $M_n$ of 10000 to 20000 g/mole. The ROP polymer chains also have a narrow polydispersity index (PDI), generally from 1.01 to 1.35, more particularly 1.1 to 1.30, and even more particularly 1.1 to 1.25.

The catalysts can be removed by selective precipitation, or in the case of the solid supported catalysts, simply by filtration. The ROP polymer can comprise residual catalyst in an amount greater than 0 wt. %, based on total weight of the first polymer and the residual catalyst. The amount of residual catalyst can also be less than 20 wt. %, less than 15 wt. %, less than 10 wt. %, less than 5 wt. %, less than 1 wt. %, or most specifically less than 0.5 wt. % based on the total weight of the first polymer and the residual catalyst.

As stated above, the ROP polymer can comprise a pendant latent carboxylic acid group, such as a benzyl ester. In this instance, the latent carboxylic acid group can be deprotected using $H_2$/Pd—C to form a pendant carboxylic acid group. If the protected carboxylic acid is in the form of a thermally labile carboxylic ester, such as a t-butyl ester, deprotection can be effected by heating the ROP polymer. If the protected carboxylic acid is hydrolytically unstable, such as a trifluoroethyl ester, the ROP polymer can be deprotected with mild aqueous acid or base to form a pendant carboxylic acid group. In a particular embodiment, the protected carboxylic acid is a benzyl ester.

Also disclosed are methods of forming compositions comprising the surface modified nanoparticles. One method comprises independently covalently attaching by a ring opening reaction a first cyclic carbonyl monomer independently to three or more nucleophilic surface groups of a nanostructure, thereby forming a first modified nanoparticle, the first modified nanoparticle comprising three or more initiator groups produced by the ring opening of the first cyclic carbonyl monomer; and independently initiating a ring opening polymerization of a mixture comprising one or more cyclic carbonyl monomers by the three or more initiator groups, thereby forming a surface modified nanoparticle comprising three or more independent surface branches, wherein each of the three or more independent surface branches comprises a first polymer produced by the ring opening polymerization; wherein the first cyclic carbonyl monomer has the general formula (12):

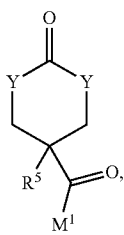
(12)

wherein each Y is independently selected from the group consisting of —O—, —NH—,

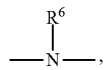

and —S—, $R^5$ and $R^6$ are independent monovalent radicals comprising 1 to 30 carbons, and $M^1$ is a monovalent radical selected from the group consisting of —$OR^1$, —$NHR^1$, —$NR^1R^1$, and —$SR^1$, wherein $R^1$ is a monovalent radical. In an embodiment, the first cyclic carbonyl monomer is a cyclic carbonate, and $M^1$ comprises a second polymer. In another embodiment, the second polymer is a poly(alkylene ether). In another embodiment, the first cyclic carbonyl monomer does not comprise a polymeric substituent. In another embodiment, one or more of the one or more cyclic carbonyl monomers comprises a functional group comprising a poly(alkylene ether). In another embodiment, each of the three or more independent surface branches comprises a repeat unit comprising a side chain comprising a monovalent leaving group, and the method further comprises treating the surface modified nanoparticle with a tertiary amine, thereby forming a second surface modified nanoparticle comprising a quaternary amine. In another embodiment, the first polymer is a block copolymer. In another embodiment, one or more of the one or more cyclic carbonyl monomers comprises a functional group selected from the group consisting of latent carboxylic acid groups, functional groups capable of reacting with a tertiary amine to form a quaternary amine, urea groups, polyether groups, and combinations thereof. In another embodiment, the nanostructure is a macromolecule selected from the group consisting of crosslinked polymers, latexes, hyperbranched polymers, dendrimers, dendrons, cyclodextrins, and combinations of the foregoing materials. In another embodiment, the nanostructure comprises an inorganic material selected from the group consisting of cobalt, iron, and combinations thereof. In another embodiment, the three or more nucleophilic surface groups are terminal amine groups, and the nanostructure is a polypropyleneimine dendrimer selected from the group consisting of DAB4, DAB8, DAB16, DAB32 and DAB64.

The above described method can further comprise forming a first aqueous mixture comprising the surface modified nanoparticle, and contacting the first aqueous mixture with a second aqueous mixture comprising a biologically active material, thereby forming a loaded nanoparticle. The method can further comprise contacting a cell with the loaded nanoparticle. Another method of preparing a loaded nanoparticle comprises contacting a first aqueous mixture comprising the above described surface modified nanoparticles with a second aqueous mixture comprising a biologically active material. In an embodiment, the biologically active material is a gene or a drug.

Another method related to forming a surface modified nanoparticle comprises independently attaching by a ring opening reaction a first cyclic carbonyl monomer to three or more nucleophilic surface groups of a nanostructure, thereby forming a first modified nanoparticle, the first modified nanoparticle comprising three or more functional groups F' and three or more initiator groups; and independently initiating by each of the three or more initiator groups a ring opening polymerization of one or more cyclic carbonyl monomers, thereby forming a surface modified nanoparticle comprising three or more independent surface branches, wherein each of the three or more independent surface branches has the general formula (3):

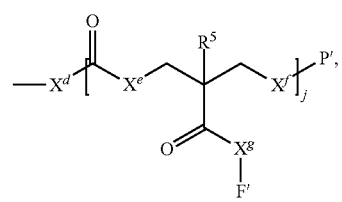
(3)

wherein $X^d$ is a divalent radical selected from the group consisting of —O—,

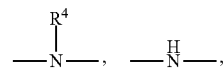

S—, and combinations thereof, $R^4$ is a monovalent radical comprising 1 to 30 carbons, j is an integer greater than or equal to 1, P' is comprises a first polymer comprising a backbone selected from the group consisting of polycarbonates, polyesters, polyureas, polycarbamates, polythiocarbamates, polythioureas, and combinations thereof, each $X^e$, $X^f$, and $X^g$ is independently selected from the group consisting of —O—,

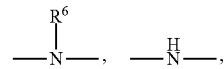

—S—, and combinations thereof, wherein $R^6$ is hydrogen or a monovalent hydrocarbon radical comprising 1 to 30 carbons, each $R^5$ is independently a monovalent hydrocarbon radical comprising 1 to 30 carbons, and each functional group F' is independently a monovalent radical.

The ROP polymer chains of the surface modified nanoparticles can comprise repeat units comprising a positive charge, a negative charge, or a mixture thereof. The ROP polymer chains can comprise from 1 to 250 mmoles carboxylic acid per gram of nanoparticles, more particularly more than 3 to 50 mmoles carboxylic acid per gram of nanoparticles, and even more particularly 3 to 40 mmoles carboxylic acid per gram of nanoparticles. The ROP polymer chains can comprise 1 to 250 mmoles of a urea functional group per gram of nanoparticles, more particularly 3 to 50 mmoles of a urea functional group per gram of nanoparticles, and even more particularly 3 to 40 mmoles of a urea functional group per gram of nanoparticles.

In aqueous solution the surface modified nanoparticles have an average particle size of from 2 nm to 500 nm, 10 nm to 250 nm, and more particularly 50 nm to 200 nm, 50 nm to 150 nm, 50 nm to 120 nm, and even more particularly from 50 nm to 100 nm, as measured by dynamic light scattering (Brookhaven Instrument Corp., Holtsville, N.Y., U.S.A.) equipped with a He—Ne laser beam at 658 nm (scattering angle:) 90°. The particle size measurements are repeated for 5 runs for each sample, and the particle size are reported as the average of 5 readings. For the foregoing particle sizes, the aqueous solution can have a pH of from 5.0 to 8.0.

Also disclosed are modified nanoparticles loaded with biologically active cargo materials, such as a gene, a nucleotide, a protein, a peptide, a drug, or combinations thereof These are referred to herein as loaded nanoparticles. In aqueous solution at a pH of from 5.0 to 8.0, the loaded nanoparticles have an average particle size of from 2 nm to 500 nm, 2 nm to 250 nm, 2 nm to 150 nm, 2 nm to 120 nm, and more particularly 10 nm to 120 nm, 20 nm to 120 nm, 30 nm to 120 nm, and even more particularly from 50 nm to 120 nm, as measured by dynamic light scattering (Brookhaven Instrument Corp., Holtsville, N.Y., U.S.A.) equipped with a He—Ne laser beam at 658 nm (scattering angle:) 90°. The particle size measurements are repeated for 5 runs for each sample, and the particle size are reported as the average of 5 readings. The loaded nanoparticles can comprise, for example 0.1 to 90 wt. %, more particularly 5 to 50 wt. %, and even more particularly 15 to 50 wt. % of a biologically active material based on total dry weight of the loaded nanoparticles. In an embodiment, the biologically active cargo material is a drug.

Also disclosed is a method of preparing a loaded nanoparticle for treating a cell, comprising contacting a first aqueous mixture comprising a modified nanoparticle comprising a surface branch comprising a ROP polymer chain derived by ring opening polymerization of one or more cyclic carbonyl monomers, with a second aqueous mixture comprising a biologically active cargo material, thereby forming a third mixture comprising the loaded nanoparticle; wherein the loaded nanoparticle has a particle size of 10 nm to 500 nm at a pH of from 5.0 to 8.0.

Further disclosed is a method of treating a cell, comprising contacting the cell with an aqueous mixture comprising the above described loaded nanoparticles. The biologically active cargo can comprise a single biologically active material or a mixture of biologically active materials. The biologically active cargo can be a drug, for example doxorubicin. Cells can be contacted in vitro, ex vivo, or in vivo. Contacting induces 0% to 20%, 0% to 15%, 0% to 10%, 0% to 5%, 0% to 2%, or more particularly 0% to 1% cytotoxicity. In an embodiment, contacting induces no cytotoxicity.

The present loaded nanoparticles can comprise both small molecular weight biologically active materials in the size range from 100 daltons to about 1,000 daltons as well as larger macromolecular materials, such as peptide and protein drugs in the size range from about 1,000 daltons to about 100,000 daltons, and beyond. Exemplary protein drugs include peptide hormones such as insulin, glucagon, parathyroid hormone, calcitonin, vasopression, renin, prolactin, growth hormone, the gonadotropins including chorionic gonadotropin, follicle stimulating hormone, thyroid stimulating hormone and leutenizing hormone; physiologically active enzymes such as transferases, hydrolases, lyases, isomerases, phosphatases, glycosidases, superoxide dismutase, factor VIII, plasminogen activators; and other therapeutic agents including protein factors such as epidermal growth factor, insulin-like growth factor, tumour necrosis factor, transforming growth factors, fibroblast growth factors, patelet-derived growth factors, erythropoietin, colony stimulating factors, bone morphogenetic proteins, interleukins and interferons. Exemplary non-protein macromolecules include polysaccharides, nucleic acid polymers, and therapeutic secondary metabolites including plant products such as vinblastine, vincristine, taxol and the like.

Other exemplary drugs include Aspirin, Diflunisal, Diclofenac, Aceclofenac, Acemetacin, Etodolac, Indometacin, Sulindac, Tolmetin, Ibuprofen, Carprofen, Fenbufen, Fenoprofen, Flurbiprofen, Ketoprofen, Ketorolac, Loxoprofen, Naproxen, Oxaprozin, Tiaprofenic acid, Suprofen, Mefenamic acid, Meclofenamic acid, Lumiracoxib, Oxyphenbutazone, Piroxicam, Lornoxicam, Meloxicam, and Tenoxicam. Steroidal Anti-Inflammatory Drugs include Hydrocortisone, Prednisone, Prednisolone, Methylprednisolone, Dexamethasone, Betamethasone, Triamcinolone, Beclometasone, Fludrocortisone acetate, and Aldosterone. Chemotherapeutic drugs include Doxorubicin and DNA alkylating Agents such as Melphalan, Chlorambucil, Dacarbazine, Temozolomide, and Streptozotocin. Antimetabolite drugs include Methotrexate, Pemetrexed, Raltitrexed, Tioguanine, Fludarabine, Pentostatin, Cladribine, Floxuridine, and Gemcitabine. Alkaloid drugs include Vincristine, Vinblastine, Vinorelbine, Vindesine, and Topoisomerase. Inhibitors include Etoposide, Teniposide, Irinotecan, and Topotecan. Taxanes include Paclitaxel and Docetaxel. Anticoagulants include Warfarin, Acenocoumarol, Phenprocoumon, Argatroban, and Ximelagatran.

Still other exemplary commercially available drugs include 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Asparaginase, ATRA, Avastin ®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone Acetate, Dexamethasone Sodium Phosphate Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, Gemzar, Gleevec™, Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan Idamycin®, Idarubicin, Ifex®, IFN-alpha Ifosfamide, IL-11 IL-2 Imatinib mesylate, Imidazole Carboxamide Interferon alfa, Interferon Alfa-2b (PEG Conjugate), Interleukin—2, Interleukin-11, Intron A® (interferon alfa-2b), Iressa®, Irinotecan, Isotretinoin, Ixabepilone, Ixempra™, K Kidrolase (t), Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Orapred®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a) Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, and Zometa.

No restriction is placed on the type of cell that can be treated with the above-described loaded nanoparticles. In particular, the cells can be eukaryotic cells, mammalian cells, and more particularly rodent or human cells. The cells can be derived from various tissues, including extraembryonic or embryonic stem cells, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, dendritic cells, neurons, glia, mast cells, blood cells and leukocytes (e.g., erythrocytes, megakaryotes, lymphocytes, such as B, T and natural killer cells, macrophages, neutrophils, eosinophils, basophils, platelets, granulocytes), epithelial cells, keratinocytes, chondrocytes, osteoblasts, osteoclasts, hepatocytes, and cells of the endocrine or exocrine glands, as well as sensory cells.

The above-described loaded nanoparticles can be used as non-viral transfection vectors. The target gene is not limited to any particular type of target gene or nucleotide sequence. For example, the target gene can be a cellular gene, an endogenous gene, an oncogene, a transgene, or a viral gene including translated and non-translated RNAs. Exemplary possible target genes include: transcription factors and developmental genes (e.g., adhesion molecules, cyclin-dependent kinase inhibitors, Wnt family members, Pax family members, Winged helix family members, Hox family members, cytokines/lymphokines and their receptors, growth/differentiation factors and their receptors, neurotransmitters and their receptors); oncogenes (e.g., ABLI, BCLI, BCL2, BCL6, CBFA2, CBL, CSFIR, ERBA, ERBB, ERBB2, ETSI, ETV6, FGR, FOS, FYN, HCR, HRAS, JUN, KRAS, LCK, LYN, MDM2, MLL, MYB, MYC, MYCLI, MYCN, NRAS, PIMI, PML, RET, SKP2, SRC, TALI, TCL3, and YES); tumor suppressor genes (e.g., APC, BRAI, BRCA2, CTMP, MADH4, MCC, NFI, NF2, RBI, TP53, and WTI); and enzymes (e.g., ACP desaturases and hydroxylases, ADP-glucose pyrophorylases, ATPases, alcohol dehydrogenases, amylases, amyloglucosidases, catalases, cyclooxygenases, decarboxylases, dextrinases, DNA and RNA polymerases, galactosidases, glucose oxidases, GTPases, helicases, integrases, insulinases, invertases, isomerases, kinases, lactases, lipases, lipoxygenases, lysozymes, peroxidases, phosphatases, phospholipases, phosphorylases, proteinases and peptidases, recombinases, reverse transcriptases, telomerase, including RNA and/or protein components, and topoisomerases).

Summarizing, surface modified nanoparticles have been described comprising surface branches comprising an ROP polymer chain derived from ring opening reaction of one or more cyclic carbonyl monomers. The ROP polymer chain can comprise a wide variety of functional groups such as biodegradable urea, quaternary amine, and/or carboxylic acid containing groups, which provide versatility in tailoring the binding strength and release properties of the loaded nanoparticles. The biologically active cargo can be of diverse size and functionality. The loaded nanoparticles can potentially be useful for delivery of small molecular drugs and proteins, and/or for simultaneous delivery of drugs and genes, or drugs and proteins.

The preparation and use of the surface modified nanoparticles based on the above-described ring opening methods is further illustrated by the following examples.

EXAMPLES

Part 1. Convergent Approach—Small Stars

Example 1

Model Reaction. Formation of MTCOMPEG, a MPEG Functionalized with a Cyclic Carbonate

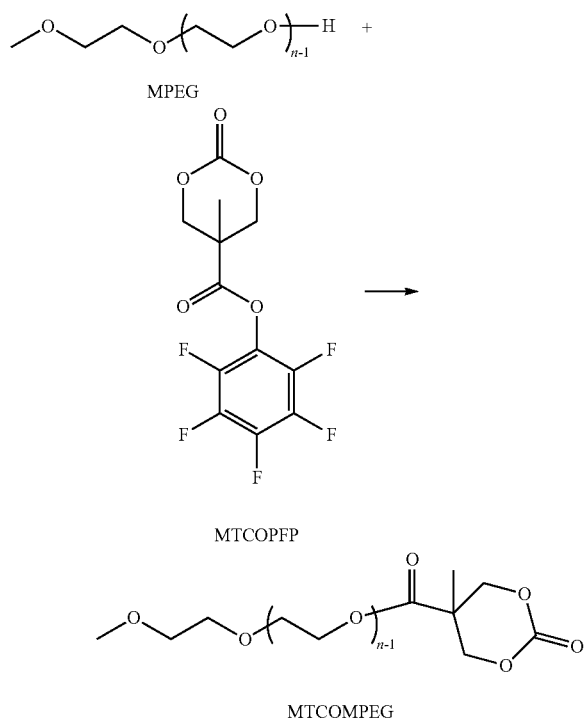

MPEG ($M_n$ 2000 g/mol, n~44, PDI 1.02, 10 g, 5 mmol, 1 eq.,) was dissolved in tetrahydrofuran (THF) (20 mL, 2.5 M) by heating the mixture. MTCOPFP (MW 326 g/mol, 3.61 g, 11 mmol, 2.2 eq.) and cesium fluoride (CsF) (MW 152 g/mol, 0.34 g, 2 mmol, 0.4 eq.) were added. After 48 hours THF was evaporated. The crude product was purified first by extraction in a mixture of dichloromethane (500 mL) and hydrochloric acid (500 mL, 0.1 M) and second by polymer precipitation in cold ethyl ether. The product MTCOMPEG was dried in vacuum until a constant weight was achieved. $M_n$=2159 g/mol, PDI=1.04. $^1$H NMR (400 MHz, CDCl$_3$): delta=4.69 (d, 8H, 4×CH$_2$OCOO), 4.31 (m, 8H, 4×PEG-CH$_2$—OCO), 4.19 (d, 8H, 4×CH$_2$OCOO), 3.84-3.44 (m, poly, 4×OCH$_2$CH$_2$ $_{PEG}$+end groups), 3.37 (s, 12H, 4×OCH$_3$), 1.33 (s, 12H, 4×CH$_3$). $^{13}$C NMR (400 MHz, CDC$_{l3}$): delta=171.0, 147.3, 72.8, 71.8, 70.8, 70.4, 68.6, 64.8, 59.0, 40.1, 30.8, 17.5

Example 2

Model Reaction. Benzylamine Ring Opening of the Cyclic Carbonate MTCOMPEG

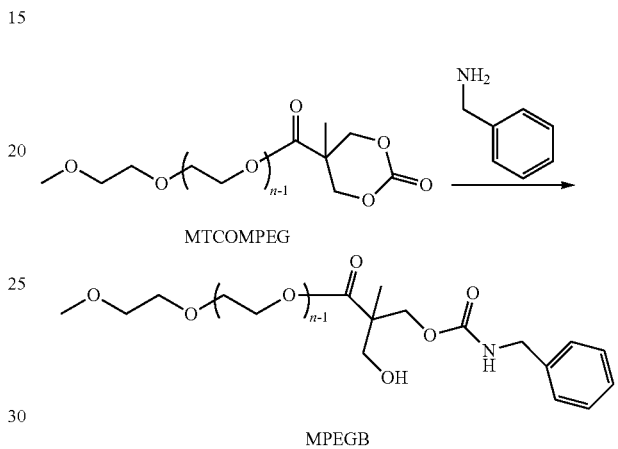

MTCOMPEG ($M_n$ 2000 g/mol, n~44, PDI 1.04, 0.5 g, 0.25 mmol, 1 eq.) was dissolved in THF (1 mL, 0.25 M) with heating. When the solution reached room temperature benzyl amine (MW 107 g/mol, 0.027 g, 0.25 mmol, 1 eq.) was added. The reaction was heated to 40° C., stirred overnight, and precipitated in cold ethyl ether. The product MPEGB was dried in vacuum until a constant weight was achieved. $M_n$=2250 g/mol, PDI=1.04. $^1$H NMR (400 MHz, CDCl$_3$): delta=7.28 (m, 5H, Ar), 4.34-4.22 (m, 6H, CH$_2$—OH+CH$_2$—OCO+Ar—CH$_2$—NHCO), 3.80-3.40 (m, poly, OCH$_2$CH$_2$ $_{PEG}$+end groups), 3.35 (s, 3H, OCH$_3$), 1.17 (s, 3H, CH$_3$). $^{13}$C NMR (400 MHz, CDCl$_3$): delta=174.2, 156.8, 138.3, 128.6, 127.4, 72.8, 70.8, 70.4, 68.7, 66.0, 64.5, 63.4, 58.9, 48.8, 44.9, 17.3

Example 3

MPEGB Reacted with Reacted with Acetyl Chloride to Form MPEGBAc

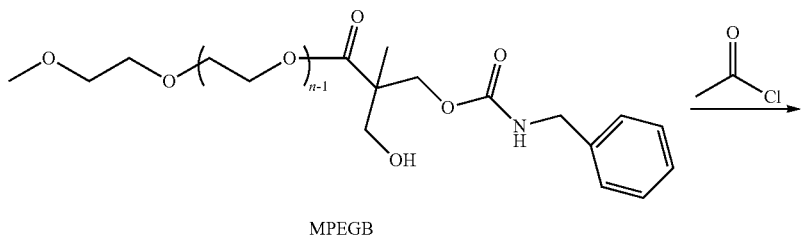

-continued

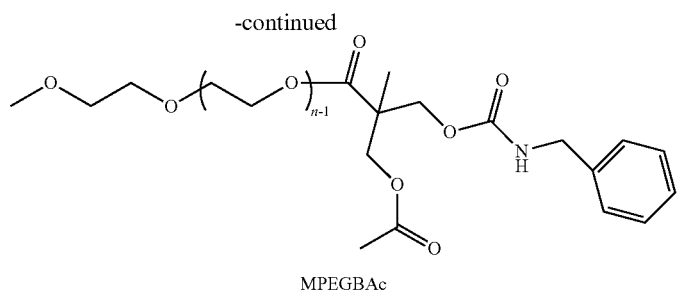

MPEGBAc

MPEGB ($M_n$ 2250 g/mol, PDI 1.04, 0.050 g, 0.03 mmol, 1 equi) was dissolved in dichloromethane (DCM) (1 mL, 0.03 M). Acetyl chloride ($M_n$ 79 g/mol, 0.002 g, 0.03 mmol, 1.2 eq.) and triethylamine (TEA) ($M_n$ 101 g/mol, 0.003 g, 0.03 mmol, 1.3 eq.) were added. After 4 hours, the solution was extracted against water. The solvent was evaporated and the product was dried in vacuum until a constant weight was achieved. $^1$H NMR (400 MHz, CDCl$_3$): delta=7.28 (m, 5H, Ar), 4.34-4.16 (m, 4H, CH$_2$—OCO+Ar—CH$_2$—NHCO), 3.84-3.42 (m, poly, OCH$_2$CH$_2$ $_{PEG}$+end groups), 3.35 (s, 3H, OCH$_3$), 2.05 (s, 2H, $\overline{CH_2}$—OCO), 1.17 (s, 3H, CH$_3$). $^{13}$C NMR (400 MHz, CDCl$_3$): δ=174.2, 156.7, 138.3, 128.7, 127.5, 71.8, 70.4, 68.8, 66.0, 64.5, 63.5, 58.9, 48.8, 44.9, 29.5, 17.3.

The above reaction models an alternative approach to constructing surface branches on nanostructures comprising three or more nucleophilic surface groups. In this approach, a first cyclic carbonyl monomer comprises a pendant ROP polymer (or another polymer such as a polyethylene glycol). The first cyclic carbonyl monomer is attached independently in a ring opening reaction to each of the three or more nucleophilic groups of a nanostructure. The initiator groups formed by the ring opening reaction (e.g., hydroxyl group) are not used to initiate a ring opening polymerization in a subsequent step. Instead, the initiator groups are derivatized with other useful functional moieties, either non-polymeric (e.g., an acetate group) or polymeric (e.g., reactive pre-formed ROP polymer or other polymer). This approach is less preferred due to steric constraints in attaching large groups to the initiator group formed by the first ring opening reaction.

Stars.

Example 4

Ring Opening of the Cyclic Carbonate MTCOMPEG with Polypropylenimine Tetraamine Dendrimer Generation 1 (DAB4) to Form Tetrol D4MPEG

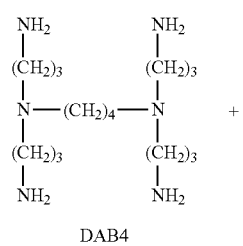

DAB4

+

-continued

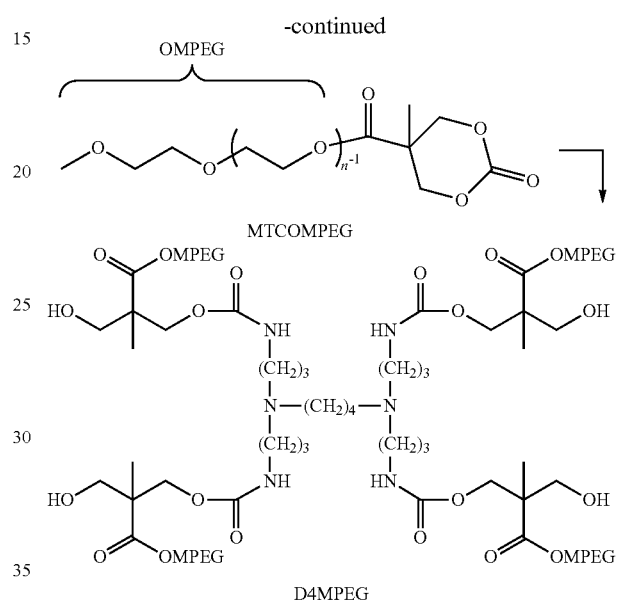

MTCOMPEG ($M_n$ 2000 g/mol, n~44, PDI 1.04, 1.0 g, 0.50 mmol, 4 eq.) was dissolved in THF (2 mL, 0.25 M) with heating. When the solution had reached room temperature DAB4 ($M_n$ 316 g/mol, 0.040 g, 0.13 mmol, 1 eq.) was added. After 40 hours the crude product was precipitated in cold ethyl ether and dried under vacuum. The product was then fractionally precipitated with dichloromethane (6 mL) as a good solvent, 2-propanol (20 mL) as semi-good solvent and ethyl ether (60 mL) as non-solvent. The product D4MPEG was filtered and dried under vacuum until a constant weight was achieved. $M_n$=8 326 g/mol, PDI=1.08. $^1$H NMR (400 MHz, CDCl$_3$): δ=5.95 (b, 4H, 4×NH—OCO), 4.30-4.10 (m, 16H, 8×CH$_2$—OCO), 3.83-3.42 (m, poly, 4×OCH$_2$CH$_2$ $_{PEG}$+ end groups), 3.73 (s, 8H, 4×CH$_2$—OH), 3.37 (s, 12H, 4×OCH$_3$), 3.18 (b, 8H, 4×CH$_2$—NH—OCO), 2.41 (b, 8H, 4×CH$_2$—N), 2.38 (b, 4H, 2×$\overline{CH_2}$—N), 1.62 (b, 8H, 4×CH$_2$), 1.42 (s, 12H, 4×CH$_3$), 1.24 (b, 4H, 2×CH$_2$—CH$_2$—N). $^{13}$C NMR (400 MHz, CDCl$_3$): δ=71.8, 70.$\overline{4}$, 68.8, 65.6, 64.2, 63.5, 58.9, 48.7, 39.8, 26.8, 25.2, 17.4.

In the following examples, the polymers are represented by the general notation:

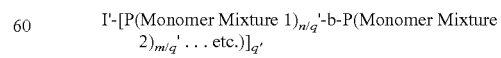

wherein I' represents a group derived from an initiator for ring opening polymerization, q' is the number of initiating sites on I', n is the total moles of cylic carbonyl monomer in Monomer Mixture 1, m is the total moles of cylic carbonyl monomer in Monomer Mixture 2, and E' is an end cap group when present. When the initiator is a polymer, it is understood that the initiator forms a block of a block copolymer, which can be indicated by insertion of "-b-" between the initiator name I' and the brackets. The brackets "[ ]" enclose the one or more polymer chain fragments formed by ring opening polymerization, "P( )" indicates a polymer formed by the one or more cyclic carbonyl monomers enclosed by the parentheses, "-r-" indicates random copolymer, and "-b-" indicates a block boundary. For example, the polymer MPEG-b-[P(MTCOEt-r-MTCU)] has the following chemical structure:

attached to the MPEG chain. The initiator and monomers have the following chemical structures.

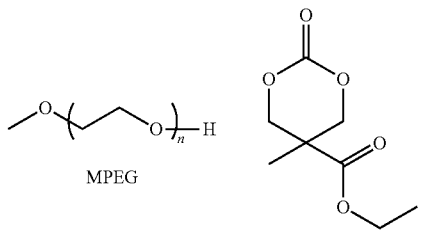

MPEG

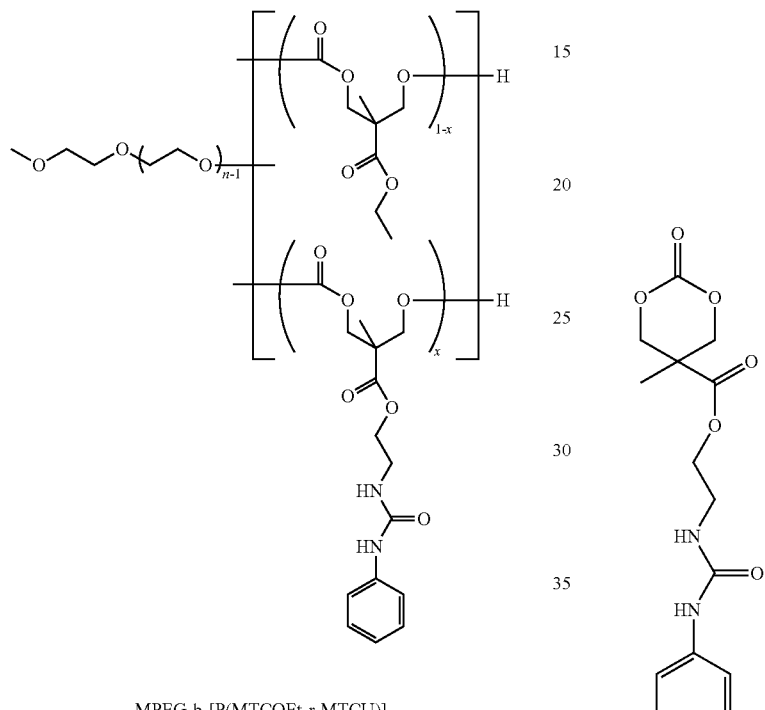

MPEG-b-[P(MTCOEt-r-MTCU)]

MPEG-b-[P(MTCOEt-r-MTCU)] comprises a hydrophilic block derived from a polyether initiator, monomethyl poly(ethylene glycol) (MPEG), and a hydrophobic block comprising a random copolymer derived from two cyclic carbonyl monomers MTCOEt and MTCU. The vertical stacking of the carbonate repeat units indicates random arrangement of the repeat units; that is, either carbonate repeat unit can be MTCOEt

MTCU

Example 5

Ring Opening Polymerization of MTCOEt Initiated by D4MPEG, DP=8

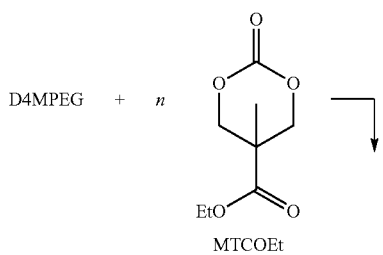

MTCOEt

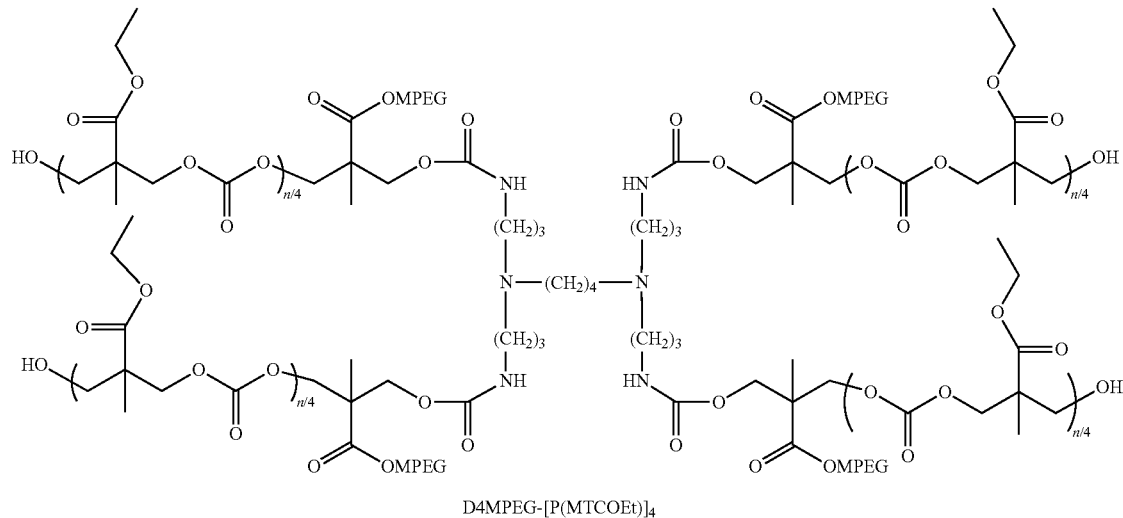

D4MPEG-[P(MTCOEt)]₄

D4MPEG was dried over CaH₂ in THF before being transferred to the glove box. D4MPEG ($M_n$ 8326 g/mol, PDI 1.08, 0.099 g, 0.01 mmol, 1 eq.) was dissolved in dry dichloromethane (1.0 mL, 1 M). DBU (MW 152 g/mol, 0.004 g, 0.02 mmol, 2 eq.) was added and reaction where stirred for 30 min. TU ($M_n$ 370 g/mol, 0.009 g, 0.02 mmol, 2 eq.) and MTCOEt ($M_n$ 188 g/mol, 0.073 g, 0.39 mmol, 32 eq.) were then added. After 2 hours the reaction was quenched with benzoic acid (MW 102 g/mol, 0.021 g, 0.21 mmol, 20 eq.) and stirred for 30 min before precipitation in ethyl ether. The product D4MPEG-[P(MTCOEt)]₄ was dried in vacuum until a constant weight was achieved. PDI=1.09. ¹H NMR (400 MHz, CDCl₃): delta=7.28 (m, 5H, Ar), 4.27 (m, poly, C—CH₂—O$_{polymer\ backbone}$), 4.17 (m, poly, CH₃—CH₂—O$_{poly(ethyl\ MTC)}$), 3.80-3.40 (m, poly, OCH₂CH₂ $_{PEG}$+end groups), 3.35 (s, 3H, OCH₃), 1.30-1.18 (m, poly, 2× CH₃ $_{poly(ethyl\ MTC)}$+end groups). ¹³C NMR (400 MHz, CDCl₃): delta=172.0, 154.5, 135.8, 128.6, 127.4, 127.2, 125.4, 72.0, 70.4, 69.0, 68.7, 68.5, 67.0, 64.5, 61.3, 61.0, 58.9, 47.0, 46.2, 34.2, 30.3, 28.6, 25.7, 21.0, 17.3, 14.0.

Part 2. Divergent Approach—Small Stars

Example 6

Ring Opening of the Cyclic Carbonate MTCU Initiated by DAB4 to Form D4PEU

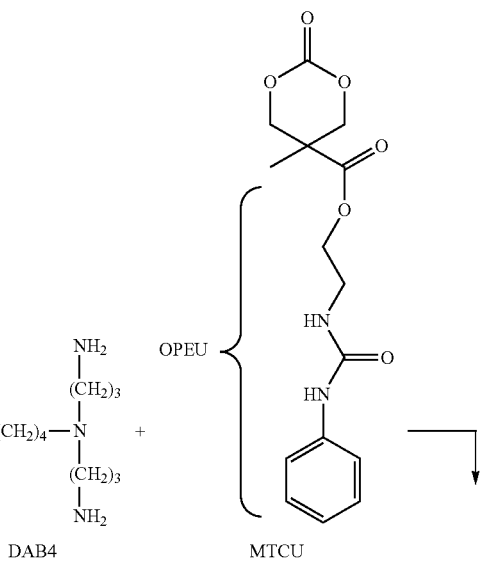

-continued

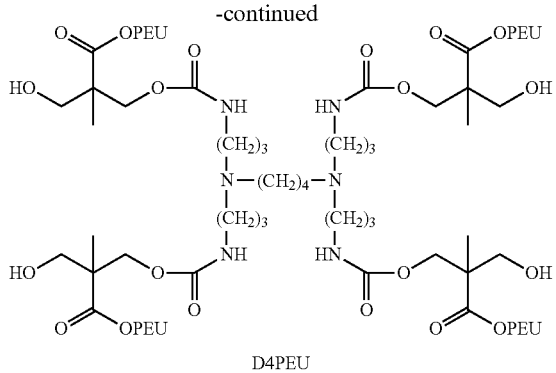

D4PEU

MTCU (MW 322 g/mol, 0.260 g, 0.81 mmol, 4.1 eq.) was dissolved in THF (10 mL, 0.08 M). DAB4 (MW 316 g/mol, 0.062 g, 0.20 mmol, 1 eq.) was added. After 72 hours calcium hydride was added. Another 24 hours later the mixture was filtrated, the solvent was evaporated, and the dry tetrol compound D4PEU was transferred to a glovebox $M_n$=1604 g/mol. $^1$H NMR (400 MHz, Acetone): delta=8.11 (s, 4H, 4×OC—NH—Ar), 7.46+7.20+6.91 (d+t+t, 20H, 4×NH—Ar), 6.67 (t, 4H, 4×OC—NH), 6.10 (b, 4H, 4×OOC—NH), 4.24-4.14 (m, 24H, 4×CH$_2$—OH+8×CH$_2$—OCO), 3.46 (m, 8H, 4×CH$_2$—NH—CONH), 3.14 (m, 8H, 4×CH$_2$—NH—COO), 2.40 (m, 12H, 6×CH$_2$—N), 1.61 (m, 8H, 4×CH$_2$), 1.42 (m, 4H, 2×CH$_2$), 1.15 (s, 12H, 4×CH$_3$).

Example 7

Ring Opening of the Cyclic Carbonate MTCOBn Initiated by DAB4 to Form D4Bn

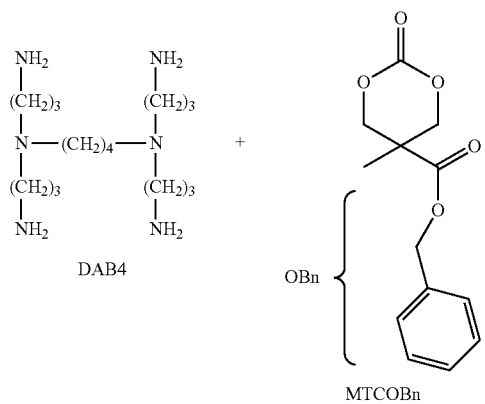

-continued

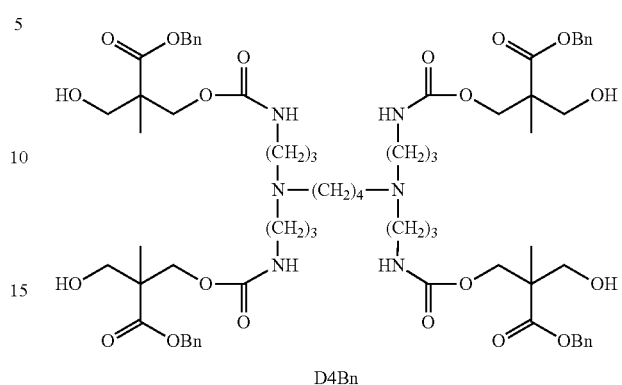

D4Bn

MTCOBn (MW 250 g/mol, 0.512 g, 2.05 mmol, 4.4 eq.) was dissolved in THF (10 mL, 0.08 M). DAB4 (MW 316 g/mol, 0.150 g, 0.47 mmol, 1 eq.) was added. After 72 hours calcium hydride was added. Another 24 hours later the mixture was filtrated, the solvent was evaporated and the dry compound D4Bn was transferred to a glovebox. $M_n$=1 317 g/mol, PDI=1.04. $^1$H NMR (400 MHz, CDCl$_3$): δ=7.38 (b, 20 H, 4×Ar), 5.90 (b, 4H, 4×OOC—NH), 5.18 (s, 8H, 4×Ar—CH$_2$—OCO), 4.38+4.21 (d+d, 16H, 4×CH$_2$—OCO), 3.70 (m, 8H, 4×CH$_2$—OH) 3.20 (m, 8H, 4×CH$_2$—NH—COO), 2.40 (m, 12H, 6×CH$_2$—N), 1.70-1.60 (m, 12H, 6×CH$_2$), 1.20 (s, 12H, 4×CH$_3$).

Example 8

Ring Opening Polymerization of MTCOEt Initiated by D4Bn to Form D4Bn-[P(MTCOEt)]$_4$, Targeted Degree of Polymerization (DP)=15

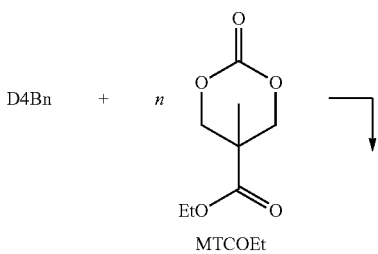

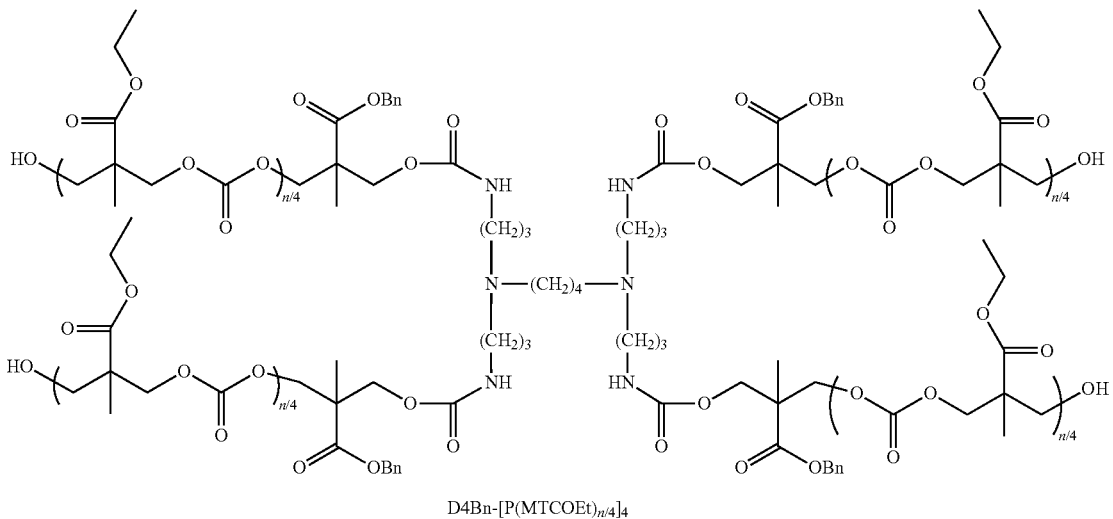

D4Bn-[P(MTCOEt)$_{n/4}$]$_4$

D4Bn (MW 1317 g/mol, 0.101 g, 0.08 mmol, 1 eq.) was dissolved in dry dichloromethane (2 mL, 2.3 M). DBU (MW 152 g/mol, 0.037 g, 0.24 mmol, 3 eq.) was added and stirred for 30 minutes. TU (MW 370 g/mol, 0.084 g, 0.23 mmol, 3 eq.) and MTCOEt (MW 188 g/mol, 0.861 g, 4.58 mmol, 60 eq.) was added. After 1.5 hours a portion of the reaction mixture was transferred to a new flask to work as an initiator for the growth of an additional block. The part that was not used for further reactions was quenched with benzoic acid and stirred for 30 min before precipitation in 2-propanol. The product D4Bn-[P(MTCOEt)$_{n/4}$]$_4$ was dried in vacuum until a constant weight was achieved. M$_n$=12597 g/mol, PDI=1.37. $^1$H NMR (400 MHz, CDCl$_3$): δ=7.32, (b, 20H, 4×Ar), 5.14 (s, 8H, 4×Ar—C$\underline{H}_2$—OCO), 4.28 (m, poly, 4×C—C$\underline{H}_2$—O$_{polymer\ backbone}$), 4.18 (m, poly, 4×CH$_3$—C$\underline{H}_2$—O$_{poly(ethyl\ MTC)}$), 3.70 (s, 8H, 4×C—C$\underline{H}_2$—OH), 1.30-1.16 (m, poly, 2×CH$_3$ $_{poly(ethyl\ MTC)}$+end groups).

Example 9

Ring Opening Polymerization of a Mixture of MTCOMPEG (M$_n$=0.5 k) and MTCOEt (Molar Ratio x:y=1:4, Respectively) Initiated by D4Bn-[P(MTCOEt)$_{n/4}$]$_4$, to form D4Bn[P(MTCOEt)$_{n/4}$-b-P(MTCOMPEG$_{x/4}$-r-MTCOEt$_{y/4}$)]

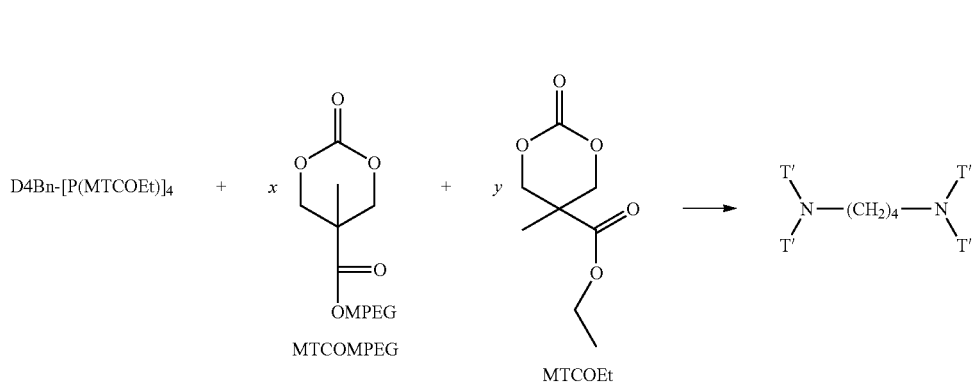

-continued

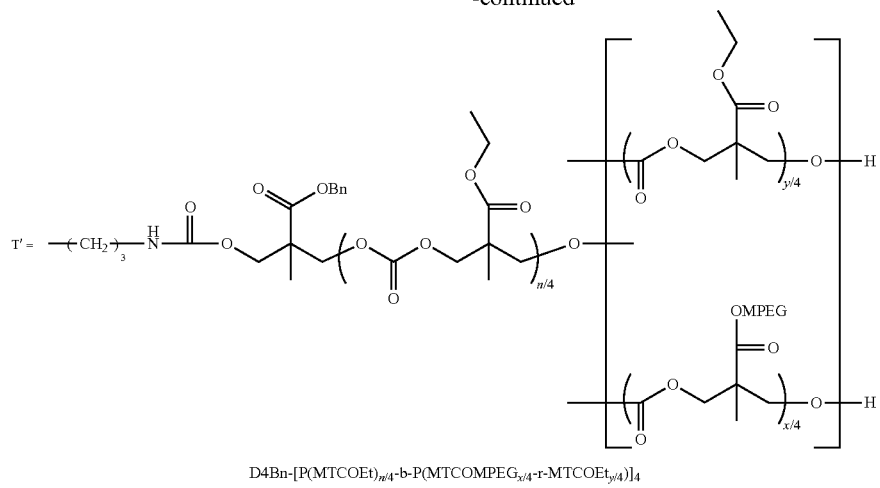

D4Bn-[P(MTCOEt)$_{n/4}$-b-P(MTCOMPEG$_{x/4}$-r-MTCOEt$_{y/4}$)]$_4$

A portion of the reaction mixture of Example 8 in its solution containing both DBU and TU was added to a new flask. The portion contained D4Bn-[P(MTCOEt)$_{n/4}$]$_4$ (M$_n$(M 12597 g/mol, PDI 1.48, 0.200 g, 0.02 mmol, 1 eq.). More DBU was added to obtain 0.1 eq. of DBU compared to the monomers MTCOMPEG and MTCOEt. MTCOMPEG (M$_n$ 659 g/mol, 0.170 g, 0.26 mmol, 16 eq.) was mixed with MTCOEt (MW 188 g/mol, 0.202 g, 1.07 mmol, 64 eq.) in DCM (2 mL). The solution of the monomers was mixed with the initiator D4Bn-[P(MTCOEt)$_{n/4}$]$_4$. After 3 hours the reaction was quenched with benzoic acid and stirred for 30 min. The product D4Bn-[P(MTCOEt)$_{n/4}$-b-P(MTCOMPEG$_{x/4}$-r-MTCOEt$_{y/4}$)]$_4$ was precipitated in ethyl ether and dried in vacuum until a constant weight was achieved. PDI=1.36 before dialysis. $^1$H NMR (400 MHz, CDCl$_3$): delta=7.32, (b, 20H, 4×Ar), 5.14 (s, 8H, 4×Ar—CH$_2$—O), 4.28 (m, poly, 4×C—CH$_2$—O$_{polymer\ backbone}$), 4.18 (m, poly, 4×CH$_3$—CH$_2$—O$_{poly(ethyl\ MTC)}$), 3.72-3.52 (m, poly, 4×OCH$_2$CH$_2$ $_{PEG}$+end groups), 3.38 (s, poly, OCH$_3$ $_{poly(PEG\ MTC)}$), 1.28-1.21 (m, poly, 2×CH$_3$ $_{poly(ethyl\ MTC)}$+end groups).

Example 10

ROP Polymerization of a Mixture of MTCOMPEG (M$_n$=0.5 k) and MTCOEt (Molar Ratio x:y=2:3, Respectively) Initiated by D4Bn[P(MTCOEt)$_{n/4}$]$_4$, Target DP=20

A portion of Example 8 in its solution containing both DBU and TU was added to a new flask, as described for Example 9. The portion contained D4Bn-[P(MTCOEt)$_{n/4}$]$_4$ (M$_n$ 12597 g/mol, PDI 1.48, 0.120 g, 0.01 mmol, 1 eq.). More DBU was added to obtain 0.1 eq. of DBU compared to the monomers. MTCOMPEG (M$_n$ 659 g/mol, 0.200 g, 0.30 mmol, 32 eq.) was mixed with MTCOEt (MW 188 g/mol, 0.086 g, 0.46 mmol, 48 eq.) in dichloromethane (2 mL, 2.3 M). The solution of the monomers was mixed with initiator D4Bn-[P(MTCOEt)$_{n/4}$]$_4$. After 3 hours the reaction was quenched with benzoic acid and stirred for 30 min. The product was precipitated in ethyl ether and dried in vacuum until a constant weight was achieved. $^1$H NMR (400 MHz, CDCl$_3$): delta=7.32 (m, 20H, 4×Ar), 5.02 (s, 8H, 4×Ar—CH$_2$—NH), 4.28 (m, poly, 4×C—CH$_2$—O$_{polymer\ backbone}$), 4.18 (m, poly, 4×CH$_3$—CH$_2$—O$_{poly(ethyl\ MTC)}$), 3.72-3.52 (m, poly, 4×OCH$_2$CH$_2$ $_{PEG}$+end groups), 3.38 (s, poly, 4×OCH$_3$ $_{poly(PEG\ MTC)}$), 1.28-1.18 (m, poly, 2×CH$_3$ $_{poly(ethyl\ MTC)}$+end groups).

Example 11

ROP Polymerization of a Mixture of MTCOMPEG (M$_n$=0.5 k) and MTCOEt (Molar Ratio x:y=1:4, Respectively) Initiated by D4Bn[P(MTCOEt)$_{n/4}$]$_4$, Target DP=40

A portion of Example 8 in its solution containing both DBU and TU was added to a new flask. The portion was equivalent to D4Bn-[P(MTCOEt)$_{n/4}$]$_4$ (M$_n$ 12597 g/mol, PDI 1.48, 0.070 g, 0.01 mmol, 1 eq.). More DBU was added to obtain 0.1 eq. of DBU compared to the monomers. MTCOMPEG (M$_n$ 659 g/mol, 0.148 g, 0.22 mmol, 40 eq.) was mixed with MTCOEt (MW 188 g/mol, 0.124 g, 0.66 mmol, 48 eq.) in dichloromethane (2 mL). The solution with the monomers was mixed with initiator D4Bn-[P(MTCOEt)$_{n/4}$]$_4$. After 3 hours the reaction was quenched with benzoic acid and stirred for 30 min. The product D4Bn[P(MTCOEt)$_{n/4}$-b-P(MTCOMPEG$_{x/4}$-r-MTCOEt$_{y/4}$)]$_4$ was precipitated in ethyl ether and dried in vacuum until a constant weight was achieved. PDI=1.20. The structure is as shown in Example 9, differing by the x:y molar ratio of 1:4, and DP=40.

Example 12

ROP Polymerization of a Mixture of MTCOMPEG (M$_n$=0.5 k) and MTCOEt (Molar Ratio x:y=1:3, Respectively) Initiated by D4Bn-[P(MTCOEt)$_{n/4}$]$_4$, Target DP=40

A portion of Example 8 in its solution containing both DBU and TU was added to a new flask. The portion was equivalent to D4Bn-[P(MTCOET)$_{n/4}$]$_4$ (M$_n$ 12597 g/mol, PDI 1.48, 0.080 g, 0.01 mmol, 1 eq.). More DBU was added to obtain 0.1 eq. of DBU compared to the monomers. MTCOMPEG (M$_n$ 659 g/mol, 0.134 g, 0.20 mmol, 32 eq.) was mixed with MTCOEt (MW 188 g/mol, 0.157 g, 0.84 mmol, 128 eq.) in dichloromethane (2 mL). The solution with the monomers was mixed with initiator D4Bn-[P(MTCOEt)$_{n/4}$]$_4$. After 3 hours the reaction was quenched with benzoic acid and stirred for 30 minutes. The product D4Bn[P(MTCOEt)$_{n/4}$-b-P(MTCOMPEG$_{x/4}$-r-MTCOEt)$_{y/4}$]$_4$ was precipitated in ethyl ether and dried in vacuum until a constant weight was achieved. PDI=1.20. The structure is as shown in Example 9, differing by the x:y molar ratio of 1:3, and DP=40. $^1$H NMR (400 MHz, CDCl$_3$): delta=7.32, (b, 20H, 4×Ar), 5.14 (s, 8H, 4×Ar—CH$_2$—O), 4.28 (m, poly, 4×C—CH$_2$—O$_{polymer\ backbone}$), 4.18 (m, poly, 4×CH$_3$—CH$_2$—O$_{poly(ethyl\ MTC)}$), 3.72-3.52 (m, poly, 4×OCH$_2$CH$_2$ $_{PEG}$+end groups), 3.38 (s, poly, OCH$_3$ $_{poly(PEG\ MTC)}$), 1.28-1.21 (m, poly, 2×CH$_3$ $_{poly(ethyl\ MTC)}$+end groups).

Example 13

ROP Polymerization of a Mixture of MTCOMPEG (M$_n$=2 k) and MTCOEt (Molar Ratio x:y=1:4, Respectively) Initiated by D4Bn-[P(MTCOEt)$_{n/4}$]$_4$, Target DP=20

A portion of Example 8 in its solution containing both DBU and TU was added to a new flask. The portion was equivalent to D4Bn-[P(MTCOEt)$_{n/4}$]$_4$ (M$_n$ 12597 g/mol, PDI 1.48, 0.200 g, 0.02 mmol, 1 eq.). More DBU was added to have 0.05 eq. of DBU compared to the monomers. MTCOMPEG (M$_n$ 2000 g/mol, 0.551 g, 0.28 mmol, 16 eq.) was mixed with MTCOEt (MW 18$^8$ g/mol, 0.189 g, 1.01 mmol, 64 eq.) in dichloromethane (2 mL). The solution with the monomers was mixed with initiator D4Bn-[P(MTCOEt)$_{n/4}$]$_4$. After 2 hours the reaction was quenched with benzoic acid and stirred for 30 min. The product D4Bn[P(MTCOEt)$_{n/4}$-b-P(MTCOMPEG$_{x/4}$-r-MTCOEt$_{y/4}$]$_4$ was precipitated in ethyl ether Example 14

ROP Polymerization of a Mixture of MTCOMPEG (M$_n$=5 k) and MTCOEt (Molar Ratio x:y=1:4, Respectively) Initiated by D4Bn-[P(MTCOEt)$_{n/4}$]$_4$, Target DP=20

A portion of Example 8 in its solution containing both DBU and TU was added to a new flask. The portion was equivalent to D4Bn-[P(MTCOEt)$_{n/4}$]$_4$ (M$_n$ 12597 g/mol, PDI 1.48, 0.047 g, 0.004 mmol, 1 eq.). More DBU was added to get 0.05 eq. of DBU compared to the monomers. MTCOMPEG (M$_n$ 5000 g/mol, 0.305 g, 0.06 mmol, 16 eq.) was mixed with MTCOEt (MW 188 g/mol, 0.045 g, 0.24 mmol, 64 eq.) in DCM (2 mL). The solution with the monomers was mixed with initiator D4Bn-[P(MTCOEt)$_{n/4}$]$_4$. After 2 hours the reaction was quenched with benzoic acid and stirred for 30 min. The product D4Bn4P(MTCOEt)$_{x/4}$-b-P(MTCOMPEG$_{x/4}$-r-MTCOEt)$_{y/4}$ was precipitated in ethyl ether and dried in vacuum until a constant weight was achieved. The structure is as shown in Example 9, differing by the x:y molar ratio of 1:4, DP=20, and M$_n$=5000 of the MPEG fragment.

Example 15

Reaction of MTCOMPEG (M$_n$=5 k) with D4Bn-[P(MTCOEt)$_{n/4}$]$_4$, DP=1

That is, the tetrol D4Bn-[P(MTCOEt)$_{n/4}$]$_4$ was endcapped with a unit of MTCOMPEG.

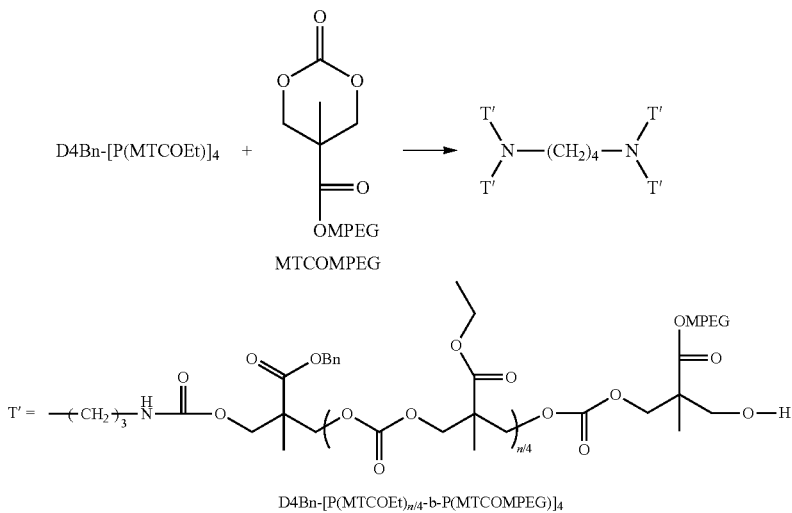

and dried in vacuum until a constant weight was achieved. PDI=1.27. The structure is as shown in Example 9, differing by the x:y molar ratio of 1:4, DP=20, and the M$_n$=2000 of the MPEG fragment. PDI=1.07. $^1$H NMR (400 MHz, CDCl$_3$): delta=7.32, (b, 20H, 4×Ar), 5.14 (s, 8H, 4×Ar—CH$_2$—O), 4.28 (m, poly, 4×C—CH$_2$—O$_{polymer\ backbone}$), 4.18 (m, poly, 4×CH$_3$—CH$_2$—O$_{poly(ethyl\ MTC)}$), 3.84-3.44 (m, poly, 4×OCH$_2$CH$_2$ $_{PEG}$+end groups), 3.38 (s, 12H, 4×OCH$_3$), 1.28-1.18 (m, poly, 2×CH$_3$ $_{poly(ethyl\ MTC)}$+end groups).

A portion of Example 8 in its solution containing both DBU and TU was added to a new flask. The portion was equivalent to D4Bn-[P(MTCOEt)$_{n/4}$]$_4$ (M$_n$ 12597 g/mol, PDI 1.48, 0.100 g, 0.01 mmol, 1 eq.). MTCOMPEG (M$_n$ 5000 g/mol, 0.240 g, 0.05 mmol, 6 eq.) was dissolved in dichloromethane (2 mL). The solution with MTCOMPEG was mixed with initiator D4Bn-[P(MTCOEt)$_{n/4}$]$_4$. After 2 hours the reaction was quenched with benzoic acid and stirred for 30 min. The product D4Bn-[P(MTCOEt)$_{n/4}$-b-P(MTCOMPEG)]$_4$ was precipitated in ethyl ether and dried in vacuum until a constant weight was achieved. PDI=1.12. $^1$H NMR (400 MHz, CDCl$_3$): delta=7.32, (b, 20H, 4×Ar), 5.14 (s, 8H, 4×Ar—CH$_2$—O), 4.28 (m, poly, 4×C—CH$_2$—O$_{polymer\ backbone}$), 4.18 (m, poly, 4×CH$_3$—CH$_2$—O$_{poly(ethyl\ MTC)}$), 3.84-3.44 (m, poly, 4×OCH$_2$CH$_2$ $_{PEG}$+end groups), 3.38 (s, 12H, 4×OCH$_3$), 1.28-1.18 (m, poly, 2×CH$_3$ $_{poly(ethyl\ MTC)}$+end groups).

Example 16

D4PEU Initiating the ROP of MTCOEt

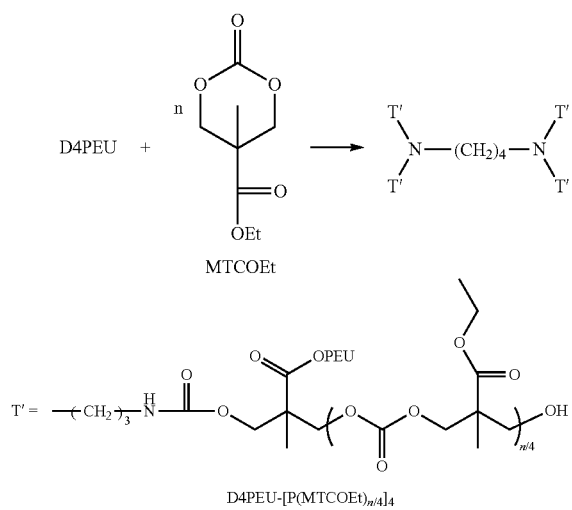

D4PEU (MW 1604 g/mol, 0.090 g, 0.01 mmol, 1 eq.) was dissolved in dry THF (1.786 mL, 1.9 M). (−)-sparteine (MW 234 g/mol, 0.042 g, 0.18 mmol, 3 eq.) was added and stirred for 30 minutes. TU (MW 370 g/mol, 0.063 g, 0.17 mmol, 3 eq.) and MTCOEt (MW 188 g/mol, 0.629 g, 3.34 mmol, 60 eq.) was added. After 5 hours the reaction was quenched with benzoic acid (MW 102 g/mol, 0.180 g, 1.8 mmol, 30 eq.). Stirred for 30 min before precipitation in 2-propanol. The product D4PEU-[P(MTCOEt)$_{n/4}$]$_4$ was dried in vacuum until a constant weight was achieved.

Part 3. Large Stars. Divergent Approach.

Example 17

Ring Opening of the Cyclic Carbonate MTCOBn Initiated by DAB4 to Form D64Bn

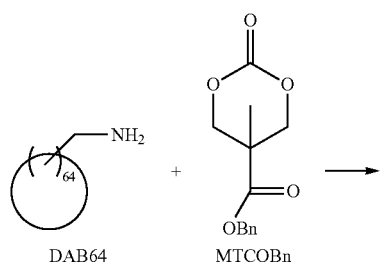

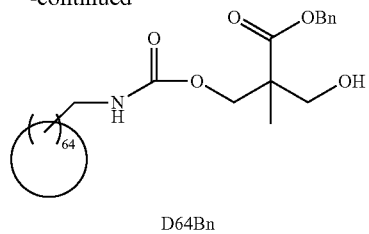

In a round bottom flask equipped with a stir bar was combined DAB64, a generation 5 polypropyleneimine based dendrimer (0.15 g) having 64 terminal amine groups and MTCOBn (0.347 g) in 3 mls of THF. The mixture was stirred overnight to give D64Bn. The reaction was heated to 50° C. for 1 hour and the reaction mixture was added to a dialysis bag and treated with methanol for 48 hours. The reaction was concentrated, redissolved in methylene chloride and stirred with CaH$_2$ for 24 hours, concentrated and stored in a glove box. $^1$H NMR (400 MHz, DMSO): delta=7.38 (b, 320 H, 4×Ar), 7.05 (b, 4H, 64×OOC—NH), 5.05 (s, 120H, 4×Ar—CH$_2$—OCO), 4.10+4.01 (d+d, 120H, 4×CH$_2$—OCO), 3.70 (m, 120H, 4×CH$_2$—OH) 3.20 (m, H, 4×CH$_2$—NH—COO), 2.40 (m, H, 6×CH$_2$—N), 1.70-1.60 (m, 12H, 6×CH$_2$), 1.20 (s, 64H, 4×CH$_3$).

Examples 18

Ring Opening Polymerization of L-Lactide Initiated by D64Bn to Form D64Bn-[P(LLA)$_{n/64}$]$_{64}$

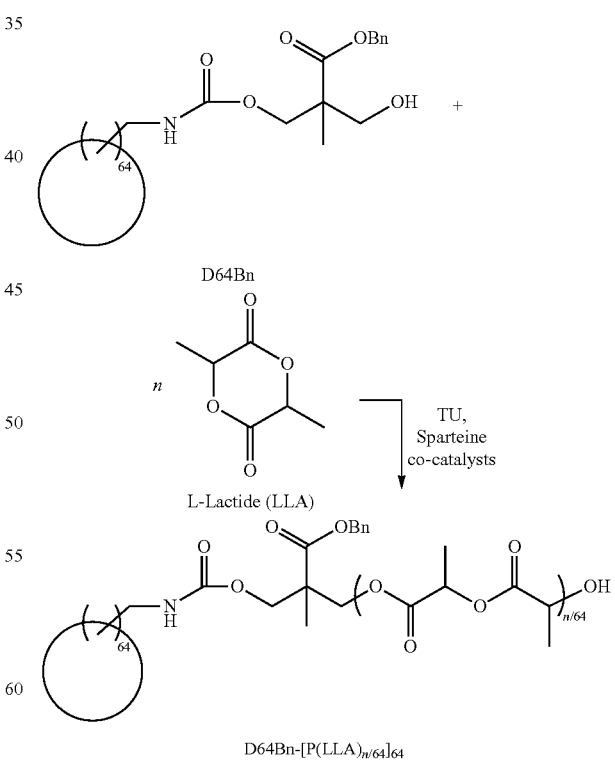

Hydroxy functional dendrimer D64Bn (10 mg) prepared in Example 17 and (−)-sparteine (0.1 mg) were dissolved in methylene chloride and stirred. In another flask TU catalyst (0.1 mg) and L-lactide (LLA) (12.0 mg) were dissolved in $CH_2Cl_2$ (1 mL) and added to the initiator flask. After 2.5 hours benzoic acid (10 mg) was added and the polymer D64Bn-[P(LLA)$_{n/64}$]$_{64}$ was precipitated in methanol. Mn=118000, PDI=1.3.

6.95 (64H, NH), 4.9 (128H, CH2 OCO), 4.30 (128H CH2ChO), 3.95 (128H CH2OH), 2.9, 2.2 and 1.5 (dendrimer core) 1.0 (192H CH3).

Example 20

Ring Opening Polymerization of L-Lactide Initiated by D64DNT to Form D64DNT-[P(LLA)$_{n/64}$]$_{64}$ Example 19

Ring Opening of the Cyclic Carbonate MTCODNT Initiated by DAB64 to Form D64DNT

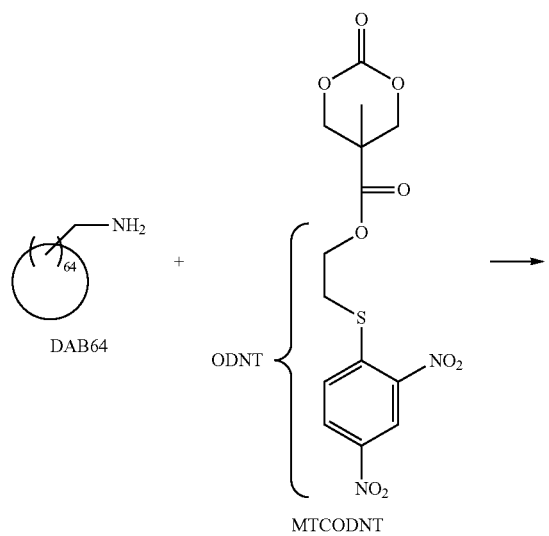

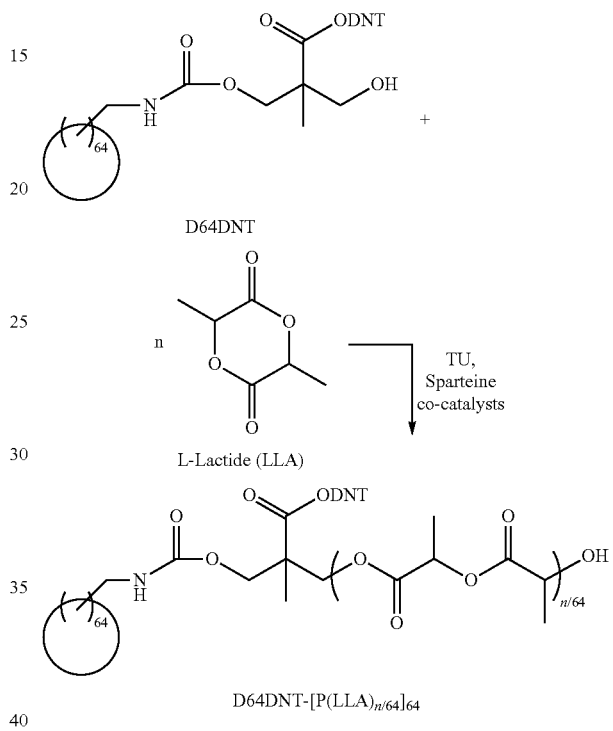

The procedure described in Example 18 was repeated using the hydroxy functional dendrimer D64DNT produced in Example 19 to form D64DNT-[P(LLA)$_{n/64}$]$_{64}$. Mn=122000, PDI=1.2.

Example 21

Ring Opening of the Cyclic Carbonate MTCU Initiated by DAB64 to Form D64PEU

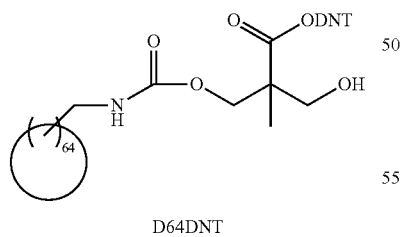

D64DNT

To a round bottom flask equipped with a stir bar, DAB64 (0.05 g) was combined together with MTCODNT (0.173 g) in THF and stirred overnight (50° C.) to give D64DNT. The reaction mixture was added to a dialysis bag and treated with methanol for 48 hours. The reaction was concentrated, redissolved in THF and stirred with $CaH_2$ for 24 hours, concentrated and stored in a glove box. $^1$H NMR (400 MHz, DMSO): δ=8.8, (64H, Ph), 8.4 (64H, Ph), 7.95 (64H, Ph),

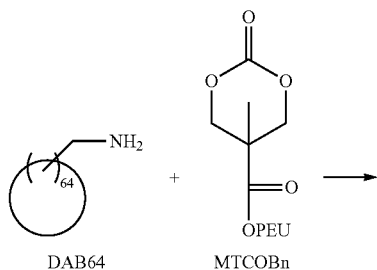

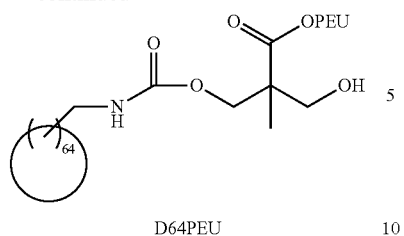

D64PEU

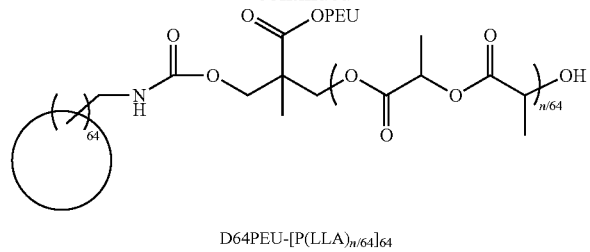

D64PEU-[P(LLA)$_{n/64}$]$_{64}$

To a round bottom flask equipped with a stir bar, DAB64 (0.15 g) was combined together with MTCU (0.1449 g) and stirred overnight (50° C.) to give D64PEU. The reaction mixture partially fell out of solution overnight and the slurry was precipitated in methylene chloride, dried and stored in the box. $^1$H NMR (400 MHz, DMSO): 8.6 (m, 64H NH), 7.4 (128H, Ph), 7.18 (128H, Ph), 7.05 (64H, CONH), 6.95 (64H, Ph), 6.2 (64H, CONHCH2), 5.05 and 4.95 (128H, CH2OCOH), 4.0-4.3 (256H, CH2OH, CH2OC), 2.95, 2.20 and 1.50 (dendrimer core).

The procedure described in Example 18 was repeated using the hydroxy functional dendrimer D64PEU produced in Example 21 to form D64PEU-[P(LLA)$_{n/64}$]$_{64}$. Mn=160000, PDI=1.18.

Part 4. Antimicrobial Star-Shaped Polymers

Example 23

Ring Opening Polymerization of L-Lactide Initiated by D4Bn to Form D4Bn-[P(LLA)$_{n/4}$]$_4$

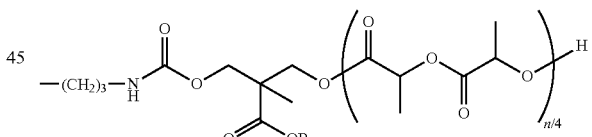

Example 22

Ring Opening Polymerization of L-Lactide Initiated by D64PEU to Form D64PEU-[P(LLA)$_{n/64}$]$_{64}$

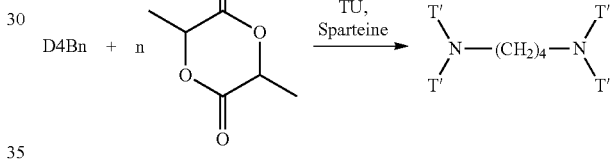

D64PEU

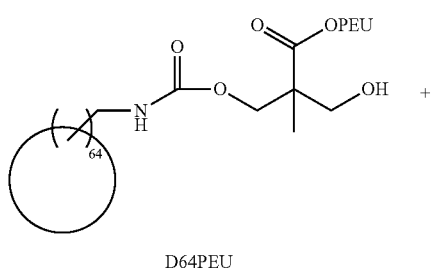

L-Lactide (LLA)

T' =

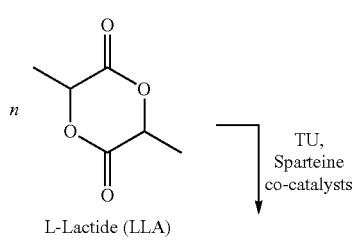

D4Bn-[P(LLA)$_{n/4}$]$_4$

D4Bn (32.6 mg, 0.02 mmol), L-lactide (LLA) (145 mg, 1.0 mmol), TU (10.6 mg, 0.03 mmol) were dissolved in dry methylene chloride (1.0 mL) and transferred to a vial containing (−)-sparteine (2.9 mg, 0.01 mmol) to conduct ROP at room temperature for 2 hours in the globe box ([LLA]/[I]= 40). Benzoic acid (11 mg, 0.09 mmol) was added to quench the reaction (~99% conversion). The mixture was stirred for 30 min, precipitated in 2-propanol, isolated, and dried in vacuum for 20 hours to yield D4Bn-[P(LLA)$_{n/4}$]$_4$ (97 mg, 55%). GPC (THF, PS standard): $M_n$=7900, PDI=1.19. $^1$H NMR (400 MHz, CDCl$_3$): delta 7.39-7.27 (m, 20H; Ph), 5.25-5.09 (m, ~80H; PhCH$_2$ and CH$_{PLA}$), 4.42-4.10 (m, 20H; OCH$_2$ and CH$_{end\ group}$), 3.23-3.06 (b, 6H; CH$_2$NH), 2.51-2.27 (b, 12H; NCH$_2$), 1.63-1.33 (m, ~263H; CH$_2$ and CH$_3$ $_{P(LLA)}$), 1.29-1.18 (m, 12H; CH$_3$).

Example 24

Ring Opening Polymerization of the Cyclic Carbonate MTCOPrBr Initiated by D4Bn-[P(LLA)$_{n/4}$]$_4$ to form D4Bn-[P(LLA)$_{n/4}$-b-P(MTCOPrBr)$_{m/4}$]$_4$

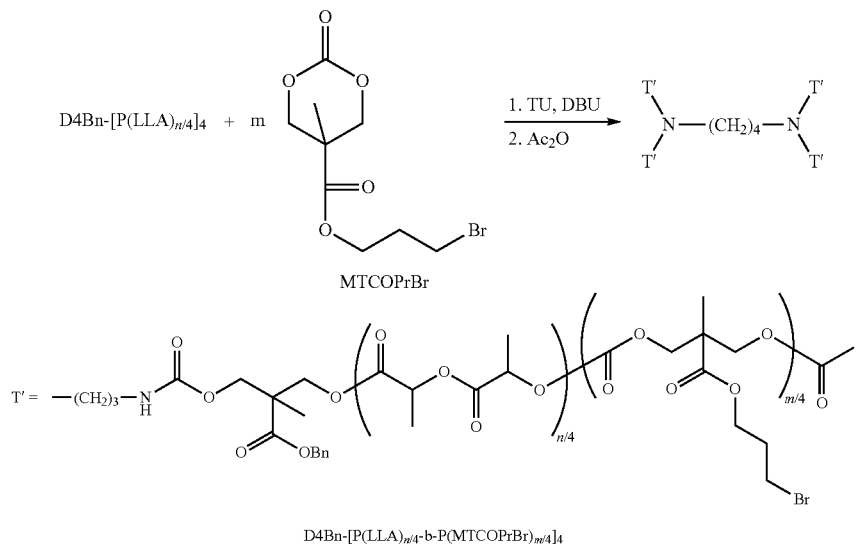

D4Bn-[P(LLA)$_{n/4}$]$_4$ (65 mg, [OH]=0.04 mmol), MTCOPrBr (126 mg, 0.45 mmol), and TU (4.1 mg, 0.01 mmol) were dissolved in dry methylene chloride (1.5 mL) and transferred to a vial containing DBU (1.9 mg, 0.01 mmol) to conduct ring openoing polymerization at room temperature for 3 hours in the globe box ([MTCOPrBr]/[OH]=11). Acetic anhydride (13 mg, 0.13 mmol) was added to the mixture in order both to quench the reaction and to cap the hydroxyl groups (~84% conversion). The mixture was stirred for 40 hours, precipitated in 2-propanol, isolated, and dried in vacuum for 50 hours to yield D4Bn-[P(LLA)$_{n/4}$-b-P(MTCOPrBr)$_{m/4}$]$_4$ (146 mg, 77%). GPC (THF, PS standard): M$_n$=15200, PDI=1.32. $^1$H NMR (400 MHz, DMSO-d$_6$): delta 7.38-7.28 (m, 20H; Ph), 5.24-5.08 (m, ~80H; PhCH$_2$ and CH$_{P(PLLA)}$), 4.45-4.11 (m, ~293H; OCH$_2$ and OCH$_{2\ P(MTCOPrBr)}$), 3.51-3.39 (m, ~91H; CH$_2$Br$_{P(MTCOPrBr)}$), 3.21-3.08 (b, 5H; CH$_2$NH), 2.48-2.32 (b, 11H; NCH$_2$), 2.24-2.14 (m, ~96H; CH$_{2\ P(MTCOPrBr)}$), 1.65-1.45 (m, ~251H; CH$_2$ and CH$_{3\ P(LLA)}$), 1.39 (b, 4H; CH$_2$), 1.30-1.18 (m, ~155H; CH$_3$ and CH$_{3\ P(MTCOPrBr)}$).

Example 25

Quaternization of D4Bn-[P(LLA)$_{n/4}$-b-P(MTCOPrBr)$_{m/4}$]$_4$

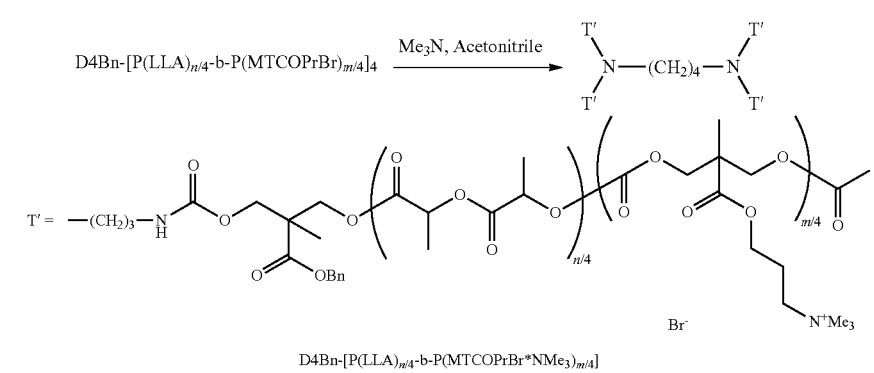

Trimethylamine gas (301 mg, 5.1 mmol) was charged to an acetonitrile solution (6 mL) of D4Bn-[P(LLA)$_{n/4}$-b-P(MTCOPrBr)$_{m/4}$]$_4$ (119 mg, [Br]=0.29 mmol) immersed in a dry-ice/acetone bath. The solution was allowed to warm to room temperature and with continued stirring for 16 hours. Then acetonitrile and excess gasses were removed from the reaction mixture under vacuum to give D4Bn[P(LLA)$_{n/4}$-b-P(MTCOPrBr*NMe$_3$)$_{m/4}$] (134 mg, 99%). M$_n$ 21800 (calculated from NMR). $^1$H NMR (400 MHz, MeOH-d$_4$): delta 7.43-7.27 (b, 20H; Ph), 5.30-5.12 (m, ~87H; PhCH$_2$ and CH$_{P(LLA)}$), 4.51-4.14 (m, ~356H; OCH$_2$ and OCH$_{2\ P(MTCOPrBr*NM3)}$), 3.64-3.44 (b, ~112H; CH$_2$Br$_{P(MTCOPrBr*NMe3)}$), 3.29-3.11 (b, ~499H; CH$_2$NH and $N^+CH_3$ $_{P(MTCOPrBr^*NMe3)}$), 2.64-2.41 (b, 7H; $NCH_2$), 2.33-2.15 (b, ~110H; $CH_2$ $_{P(MTCOPrBr^*NMe3)}$), 1.63-1.37 (m, ~291H; $CH_2$ and $CH_3$ $_{P(LLA)}$), 1.39-1.18 (m, ~192H; $CH_3$ and $CH_3$ $_{P(MTCOPrBr^*NMe3)}$).

Surface Modified Inorganic Nanoparticles.

Example 26

Synthesis of $CoFe_2O_4$ Nanoparticles

In a flask, 2 mmol $Fe(acac)_3$, 1 mmol $Co(acac)_2$, 10 mmol 1,2-hexadecanediol, 6 mmol oleic acid, 6 mmol oleylamine, and 20 mL of benzyl ether were combined and mechanically stirred under a flow of $N_2$. The mixture was heated to 200° C. for 2 hours and then, under a blanket of $N_2$, heated to reflux (~300° C.) for 1 hour. The black colored mixture was cooled to room temperature by removing the heat sources. Under ambient conditions, 40 mL of ethanol was added to the mixture and a black material was precipitated and separated via centrifugation at 6000 rpm for 10 minutes. The black precipitate was dissolved in hexane with 0.1% oleic acid. The mixture was centrifuged at 6000 rpm for 10 minutes to remove any undispersed residue. The product was then precipitated with ethanol, centrifuged to remove the solvent, and dried in vacuum overnight. The average diameter of the $CoFe_2O_4$ nanoparticles is 6 nm with narrow size distribution. The as-synthesized 6 nm $CoFe_2O_4$ nanoparticles were further used as the seeds to grow larger particles. Typically, 2 mmol $Fe(acac)_3$, 1 mmol $Co(acac)_2$, 10 mmol 1, 2-hexadecanediol, 2 mmol oleic acid, 2 mmol oleylamine, and 20 mL of benzyl ether were mixed and mechanically stirred under a flow of $N_2$. 6 mL of the above synthesized 6 nm $CoFe_2O_4$ nanoparticle hexane solution (15 mg/mL) was added. The mixture was first heated to 100° C. for 30 min to remove hexane, and then increased to 200° C. for 1 hour. Under a blanket of $N_2$, the mixture was further heated to 300° C. for 30 min. Following the same workup procedures, the monodispersed $CoFe_2O_4$ nanoparticles with a diameter of 15 nm were obtained. Finally, this seed mediated growth method was repeated again to prepare 18 nm monodispersed $CoFe_2O_4$ nanoparticles.

Example 27

Silica Shell-Coated $CoFe_2O_4$ Nanoparticle with Amine Functionalized Surface

In a glass container under ambient conditions, 1 mL of polyacrylic acid (PAA) in THF (10 mg/mL) was added to a dispersion of above synthesized 18 nm $CoFe_2O_4$ Nanoparticles (10 mg in 10 mL). The mixture was shaken for 2 hours with occasional sonication. The modified particles were separated with a magnet and the solvent was decanted. The particles were washed three times with hexane and methanol to remove the free oleic acid and excess PAA polymer. The washed particles were dispersed in aqueous solution by ionizing the carboxylic groups with a dilute NaOH solution. Then, 1.5 mL of PAA modified $CoFe_2O_4$ nanoparticle aqueous solution was mixed with ethanol (10 mL), and ammonium hydroxide (30 wt %, 400 microliters) by vigorous mechanical stirring. Tetraethoxy silane (TEOS)/ethanol solution (200 microliters, 10 mM) was added to the mixture every 2 hours until the total amount of TEOS solution reached 1 mL. After obtaining the desired size, aminopropyl triethoxysilane was added to the solution. The amine-functionalized silica coated $CoFe_2O_4$ nanoparticles were collected by magnetic separation, and washed with ethanol three times, and finally dispersed in THF.

Example 28

Ring Opening Reaction of MTCOMPEG with Amine-Functionalized Silica Coated $CoFe_2O_4$ Nanoparticles (Example 27)

MTCOMPEG ($M_n$ 2000 g/mol, n ~44, PDI 1.04, 50 mg, 0.025 mmol) was added to a suspension of the amine-functionalized silica coated $CoFe_2O_4$ nanoparticles in THF. The reaction was heated to dissolve the MTCOMPEG then stirred for 16 hours at ambient temperature. The functionalized nanoparticles were collected by centrifugation.

Example 29

Ring Opening Polymerization of L-Lactide from MTCOMPEG Functionalized $CoFe_2O_4$ Nanoparticles (Example 28)

A solution of MTCOMPEG-functionalized nanoparticles from Example 28 in dichloromethane (1 mL) was transferred into the glove box. L-Lactide (12.7 mg), 10 microliters of a thiourea catalyst solution (15.4 mg/mL in dichloromethane), and 10 microliters of a DBU solution (5.9 mg/mL in dichloromethane) were added to the solution of MTCOMPEG-functionalized nanoparticles. The reaction mixture was stirred at ambient temperature for 16 hours, then quenched with benzoic acid (MW 102 g/mol, 0.021 g, 0.21 mmol, 20 eq.). The product $CoFe_2O_4$-MPEG-[P(LLA)] was isolated by centrifugation.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A composition, comprising:
   a surface modified nanoparticle comprising:
   a core comprising a material selected from the group consisting of organic materials, organometallic materials, inorganic materials, metals, metal oxides, and combinations thereof; and
   a surface branch covalently linked to the core having the general formula (3):

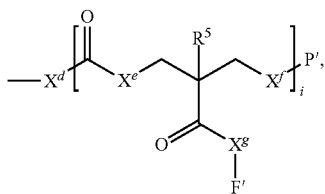
(3)

wherein
$X^d$ is selected from the group consisting of —O—,

—S—, and combinations thereof, wherein $R^4$ is a monovalent radical comprising 1 to 30 carbons,
j is an integer greater than or equal to 1,
each of $X^e$, $X^f$, and $X^g$ is independently selected from the group consisting of —O—,

and —S—, wherein $R^6$ is selected from the group consisting of hydrogen and monovalent hydrocarbon radicals comprising 1 to 30 carbons,
P' comprises a first polymer comprising a backbone selected from the group consisting of polycarbonates, polyesters, polyureas, polycarbamates, polythiocarbamates, polythioureas, and combinations thereof,
each $R^5$ is independently selected from the group consisting of hydrogen, and monovalent hydrocarbon radicals comprising 1 to 30 carbons, and
each F' is independently a monovalent radical.

2. The composition of claim 1, wherein $X^e$ and $X^f$ are —O—, and j is 1.

3. The composition of claim 1, wherein P' comprises a substituent group selected from the group consisting of urea groups, carboxylic acid groups, carboxylic acid salts, latent carboxylic acid groups, quaternary amine groups, tertiary amine groups, poly(alkylene ether) groups, and combinations thereof.

4. The composition of claim 1, wherein each F' independently comprises a substituent group selected from the group consisting of urea groups, carboxylic acid groups, latent carboxylic acid groups, quaternary amine groups, tertiary amine groups, poly(alkylene ether) groups, and combinations thereof.

5. The composition of claim 1, wherein F' is hydrogen.

6. The composition of claim 1, wherein F' comprises a poly(alkylene ether) chain, and P' comprises a backbone selected from the group consisting of polyester, polycarbonate, and combinations thereof.

7. The composition of claim 1, further comprising a biologically active material.

8. The composition of claim 7, wherein the biologically active material is a gene or a drug.

9. A method of preparing a loaded nanoparticle, comprising contacting a first aqueous mixture comprising the composition of claim 1 with a second aqueous mixture comprising a biologically active material.

10. The method of claim 9, wherein the biologically active material is a gene or a drug.

11. The composition of claim 1, wherein the core is an organic core and $X^d$ is

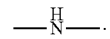.

12. The composition of claim 11, wherein the organic core consists of carbon, hydrogen and nitrogen.

13. The composition of claim 1, wherein the core is an inorganic core comprising cobalt and/or iron.

14. The composition of claim 13, wherein $X^e$ and $X^f$ are —O—, and P' comprises a backbone selected from the group consisting of polycarbonate, polyester, and combinations thereof.

15. The composition of claim 1, wherein $X^g$ is —O— and F' comprises a poly(alkylene) ether chain comprising a —CH$_2$CH$_2$O— repeat unit.

16. The composition of claim 1, wherein P' comprises a polylactide chain.

17. A method, comprising:
attaching by a ring opening reaction a first cyclic carbonyl monomer to a nucleophilic surface group of a nanostructure, thereby forming a first modified nanoparticle, the first modified nanoparticle comprising a functional group F' and an initiator group; and
initiating by the initiator group a ring opening polymerization of one or more cyclic carbonyl monomers, thereby forming a surface modified nanoparticle comprising i) a core comprising a material selected from the group consisting of organic materials, organometallic materials, inorganic materials, metals, metal oxides, and combinations thereof and ii) a surface branch covalently linked to the core having the general formula (3):

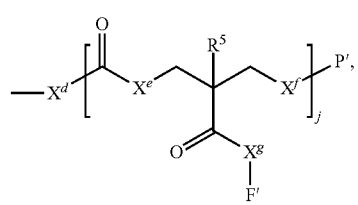
(3)

wherein
$X^d$ is selected from the group consisting of —O—,

—S—, and combinations thereof, wherein $R^4$ is a monovalent radical comprising 1 to 30 carbons,
j is an integer greater than or equal to 1,
each of $X^e$, $X^f$, and $X^g$ is independently selected from the group consisting of —O—,

and —S—, wherein $R^6$ is selected from the group consisting of hydrogen and monovalent hydrocarbon radicals comprising 1 to 30 carbons, P' comprises a first polymer comprising a backbone selected from the group consisting of polycarbonates, polyesters, polyureas, polycarbamates, polythiocarbamates, polythioureas, and combinations thereof, each $R^5$ is independently selected from the group consisting of hydrogen, and monovalent hydrocarbon radicals comprising 1 to 30 carbons, and each F' is independently a monovalent radical.

18. The method of claim 17, wherein i) the nanostructure comprises three or more nucleophilic surface groups and ii) the first modified nanoparticle comprises three or more functional groups F' and three or more initiator groups.

19. The method of claim 18, wherein each of the three or more initiator groups independently initiates a ring opening polymerization of the one or more cyclic carbonyl monomers.

20. The method of claim 17, wherein the core is an organic core and $X^d$ is

21. The method of claim 20, wherein the organic core consists of carbon, hydrogen and nitrogen.

22. The method of claim 17, wherein the core is an inorganic core comprising cobalt and/or iron.

23. The method of claim 22, wherein $X^e$ and $X^f$ are —O—, and P' comprises a backbone selected from the group consisting of polycarbonate, polyester, and combinations thereof.

24. The method of claim 17, wherein $X^g$ is —O— and F' comprises a poly(alkylene) ether chain comprising a —$CH_2CH_2O$— repeat unit.

25. The method of claim 17, wherein P' comprises a polylactide chain.

26. The method of claim 17, wherein the first cyclic carbonyl monomer is a cyclic carbonate, and F' comprises a second polymer.

27. The method of claim 26, wherein the second polymer is a poly(alkylene ether).

28. The method of claim 17, wherein the nanostructure is a dendrimer selected from the group consisting of DAB4, DAB8, DAB16, DAB32, DAB64, and combinations thereof.

* * * * *